(12) United States Patent
Uber, III et al.

(10) Patent No.: US 11,246,558 B2
(45) Date of Patent: *Feb. 15, 2022

(54) QUANTIFICATION PHANTOM FOR USE WITH MULTIPLE IMAGING MODALITIES

(71) Applicant: BAYER HEALTHCARE LLC, Whippany, NJ (US)

(72) Inventors: Arthur Uber, III, Pittsburgh, PA (US); Kevin Cowan, Allison Park, PA (US); David Griffiths, Pittsburgh, PA (US); Ivana Kingston, Pittsburgh, PA (US); Dzmitry Liushtyk, Richmond Hill (CA); Matthew Hoiko, Toronto (CA); Roey Flor, Pittsburgh, PA (US); Robert Redmond, Kingston (CA); Henry Hernaez, Pittsburgh, PA (US); Sridhar Balasubramanian, Mars, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/710,118

(22) Filed: Dec. 11, 2019

(65) Prior Publication Data

US 2020/0146647 A1 May 14, 2020

Related U.S. Application Data

(62) Division of application No. 15/553,317, filed as application No. PCT/US2016/019893 on Feb. 26, 2016, now Pat. No. 10,507,003.

(Continued)

(51) Int. Cl.
*A61B 6/00* (2006.01)
*G01T 7/00* (2006.01)
(Continued)

(52) U.S. Cl.
CPC .......... *A61B 6/583* (2013.01); *A61B 5/0035* (2013.01); *A61B 5/055* (2013.01); *A61B 6/032* (2013.01);
(Continued)

(58) Field of Classification Search
CPC ........ A61B 6/488; A61B 6/50; A61B 6/5235; A61B 6/5258; A61B 6/527; A61B 6/5288;
(Continued)

(56) References Cited

U.S. PATENT DOCUMENTS 4,233,507 A 11/1980 Volz
4,499,375 A 2/1985 Jaszczak
(Continued)

FOREIGN PATENT DOCUMENTS

EP 0082733 A1 * 6/1983 ............. A61B 6/583
WO 2016134275 A1 8/2016

OTHER PUBLICATIONS

Pfanner et al. Monitoring cardiac motion in CT using a continuous wave radar embedded in the patient table, Aug. 21, 2014, Med. Phys., vol. 41, pp. 1-10. (Year: 2014).*

(Continued)

*Primary Examiner* — Christine S. Kim
(74) *Attorney, Agent, or Firm* — David Schramm; Joseph L. Kent; James R. Stevenson

(57) ABSTRACT

Described is an in-scan phantom for use during an imaging procedure. The phantom can include at least one measuring insert and/or at least one measured insert. The measuring insert may have radiation detecting capabilities while the measured insert may include a radioactive material. Also described is an imaging modality system that includes an (Continued)

imaging modality and an in-scan phantom as well as methods of using the in-scan phantom for imaging a patient or performing a scout scan.

9 Claims, 12 Drawing Sheets

Related U.S. Application Data

(60) Provisional application No. 62/121,835, filed on Feb. 27, 2015.

(51) Int. Cl.
| | |
|---|---|
| *A61B 5/055* | (2006.01) |
| *G01R 33/48* | (2006.01) |
| *G01R 33/58* | (2006.01) |
| *A61B 8/00* | (2006.01) |
| *A61B 6/03* | (2006.01) |
| *A61B 5/00* | (2006.01) |
| *G01T 1/29* | (2006.01) |
| *A61B 6/10* | (2006.01) |
| *A61B 6/04* | (2006.01) |

(52) U.S. Cl.
CPC ............ *A61B 6/037* (2013.01); *A61B 6/4417* (2013.01); *A61B 6/488* (2013.01); *A61B 6/50* (2013.01); *A61B 6/527* (2013.01); *A61B 6/5235* (2013.01); *A61B 6/5258* (2013.01); *A61B 6/5288* (2013.01); *A61B 6/544* (2013.01); *A61B 6/545* (2013.01); *A61B 6/585* (2013.01); *A61B 8/587* (2013.01); *G01R 33/481* (2013.01); *G01R 33/58* (2013.01); *G01T 1/2985* (2013.01); *G01T 7/00* (2013.01); *A61B 6/0442* (2013.01); *A61B 6/107* (2013.01); *A61B 6/482* (2013.01); *A61B 6/563* (2013.01); *A61B 8/00* (2013.01)

(58) Field of Classification Search
CPC ......... A61B 6/544; A61B 6/545; A61B 6/585; A61B 8/587; G01R 33/481; G01R 33/58; G01T 1/2985; G01T 7/00
See application file for complete search history.

(56) References Cited

U.S. PATENT DOCUMENTS

| | | | |
|---|---|---|---|
| 4,724,110 A | | 2/1988 | Arnold |
| 4,782,502 A | * | 11/1988 | Schulz ................... A61B 6/032 250/252.1 |
| 5,034,969 A | * | 7/1991 | Ozaki ................... A61B 6/583 378/162 |
| 5,506,884 A | | 4/1996 | Goodenough et al. |
| 5,521,955 A | * | 5/1996 | Gohno ................... A61B 6/505 378/18 |
| 5,841,835 A | | 11/1998 | Aufrichtig et al. |
| 6,987,270 B2 | | 1/2006 | Trotter et al. |
| 8,186,880 B1 | * | 5/2012 | Arnold ................... A61B 6/032 378/18 |
| 2004/0167387 A1 | | 8/2004 | Wollenweber et al. |
| 2005/0031080 A1 | * | 2/2005 | Klingenbeck-Regn ..................... A61B 6/545 378/95 |
| 2006/0153341 A1 | | 7/2006 | Guyonnet et al. |
| 2008/0240364 A1 | | 10/2008 | Main et al. |
| 2008/0298540 A1 | | 12/2008 | Serban et al. |
| 2010/0167251 A1 | | 7/2010 | Boutchko et al. |
| 2012/0150505 A1 | | 6/2012 | Couch et al. |
| 2013/0006649 A1 | * | 1/2013 | Rangadass ............. G16H 70/60 705/2 |
| 2013/0033700 A1 | * | 2/2013 | Hallil ................... A61N 5/1071 356/72 |
| 2013/0195255 A1 | * | 8/2013 | Avila ..................... A61B 6/583 378/207 |
| 2013/0228696 A1 | | 9/2013 | McGregor et al. |
| 2014/0294140 A1 | | 10/2014 | Kirby et al. |
| 2015/0087959 A1 | * | 3/2015 | Ler ...................... A61B 5/7217 600/411 |
| 2017/0347987 A1 | | 12/2017 | Hong et al. |

OTHER PUBLICATIONS

"Extended European Search Report from EP App. No. 16756489", dated Dec. 19, 2018.

"International Search Report and the Written Opinion from PCT Application No. PCT/US2016/019893", dated Jun. 3, 2016.

Jansen; et al., "Kinetic Curves of Malignant Lesions Are Not Consistent Across MRI Systems: Need for Improved Standardization of Breast Dynamic Contrast-Enhanced MRI Acquisition", AJR, Sep. 2009, 193.

Pineda, Federico , "Improvements in Diagnostic Accuracy with Quantitative Dynamic Contrast Enhanced MRI"., Award No. W81XWH-11-1-0042., Report Date: Dec. 2012.

Primak; et al., "Noninvasive Differentiation of Uric Acid versus Non-Uric Acid Kidney Stones Using Dual-Energy CT", Acad Radiol., Dec. 2007,14(12), 1441-1447.

Vidal Melo Marcos F.; et al., "Quantification of Regional Ventilation—Perfusion Ratios with PET", J Nucl Med, Dec. 2003, 44, 1982-1991.

* cited by examiner

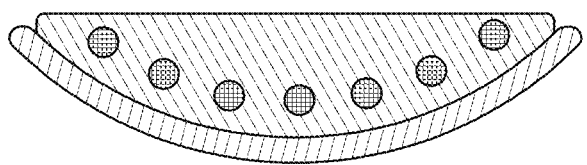
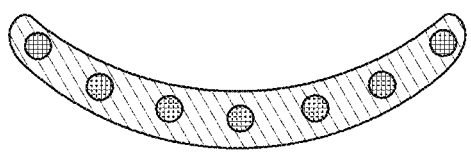
FIG. 1A  FIG. 1B
PRIOR ART
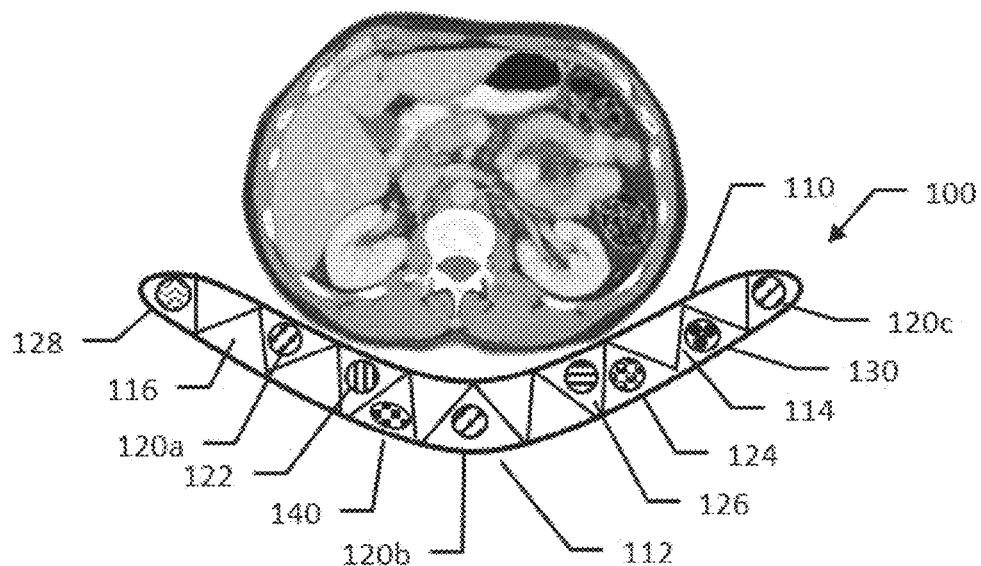
FIG. 2

QUANTIFICATION PHANTOM FOR USE WITH MULTIPLE IMAGING MODALITIES

CROSS REFERENCE TO RELATED APPLICATIONS

This application is a divisional application of U.S. application Ser. No. 15/553,317, which was filed on Aug. 24, 2017, which is a U.S. national stage filing under 35 U.S.C. § 371 of International Application No. PCT/US2016/019893, filed Feb. 26, 2016, which claims priority to U.S. Provisional Patent Application No. 62/121,835 filed on Feb. 27, 2015, the entire contents of which are expressly incorporated herein by reference.

BACKGROUND OF THE DISCLOSURE

Field of the Disclosure

This disclosure is directed to quantification phantoms that are typically used in medical imaging operations, such as computed tomography (CT), magnetic resonance imaging (MRI), positron emission tomography (PET), nuclear medicine, optical, ultrasound, and combinations thereof. More particularly, this disclosure is directed to the use of quantification phantoms which include one or more inserts or elements that allow for enhanced information collection across a wide range of operating conditions.

Description of Related Art

Early CT machines had many sources of variation in their measurement and creation of images. Calibration phantoms were often used periodically during the week to calibrate the output image calculations in Hounsfield Units (HU). A difficulty with this method is that things could change over time or from patient to patient without the operator or the radiologist knowing, because the phantoms, see FIGS. 1A, 1B, could not be used during the patient scan. The use of in-scan phantoms to resolve this problem is discussed in U.S. Pat. No. 4,233,507 issued in 1980, which is expressly incorporated herein by reference in its entirety.

As CT machines improved, the need and desire for in-scan phantoms largely went away because the operation of these machines became more stable. Moreover, since the patient was positioned between the beam source and the in-scan phantom, additional radiation to the patient was required to image the phantom and the patient. In addition, the focus of many equipment manufactures and radiologists was on achieving an image quality to allow diagnosis by a human observer rather than on the objective measures an in-scan phantom could provide. However, certain in-scan phantoms were and are still used as Quantitative Computed Tomography (QCT) phantoms because the desired accuracy and precisions of the quantitative measurement is high when measuring bone mineral density to assess osteoporosis.

Recently there have been efforts to eliminate the need for these phantoms for bone densitometry measurement by using measurements of bone, air in the esophagus or outside the patient, and one or two types of tissue that are relatively consistent from patient to patient, for example larger regions of muscle and fat.

However, given that a CT and other imaging modalities are being used more and more to assess the response to a treatment of a patient over time, it is necessary to ensure that changes in the tumor or tissue of interest that are measured between images taken at different times, optionally on different imagers with different protocols and reconstruction algorithms, really represent changes in the patient's condition and are not corrupted by differences in the imaging process itself. In addition, there are many factors which can affect the imaging process.

By having known materials with known properties in a sufficient number of the images, linear and non-linear corrections can be made to the quantitative measurements or qualitative images. At the very least, the user or reader may be alerted that something other than the patient physiology has changed as well.

SUMMARY

In accordance with some aspects, described is an in-scan phantom for use during an imaging procedure, wherein the phantom includes at least one measuring insert.

In accordance with other aspects, described is an in-scan phantom for use in an imaging procedure, wherein the phantom includes at least one measured insert that includes a radioactive material.

In accordance with other aspects, described is an imaging modality system that includes an imaging modality and an in-scan phantom that includes at least one measuring insert and/or at least one measured insert that includes a radioactive material.

In accordance with other aspects, described is a method that includes placing a patient within an imaging modality of an imaging modality system wherein the imaging modality also contains an in-scan phantom that includes at least one measuring insert and/or at least one measured insert that includes a radioactive material and imaging the patient and the in-scan phantom using the imaging modality.

In accordance with other aspects, described is a method that includes placing a patient within an imaging modality of an imaging modality system wherein the imaging modality also contains an in-scan phantom that includes at least one measuring insert and/or at least one measured insert that includes a radioactive material and performing a scout scan using the imaging modality.

Various aspects of the present disclosure may be further characterized by one or more of the following clauses:

Clause 1. An in-scan phantom for use during an imaging procedure, the phantom comprising: at least one measuring insert.

Clause 2. The in-scan phantom of clause 1, further comprising at least one measured insert.

Clause 3. The in-scan phantom of clause 2, wherein the measured insert comprises a radioactive material.

Clause 4. The in-scan phantom of clause 3, wherein the radioactive material is a positron emitter.

Clause 5. The in-scan phantom of clause 3, wherein the measured insert comprising the radioactive material is of a shorter length than at least one other measured insert of the phantom.

Clause 6. The in-scan phantom of clause 3, wherein the measured insert comprising the radioactive material is configured to move along a Z-axis of the phantom as the imaging procedure occurs.

Clause 7. The in-scan phantom of clause 3, wherein the measured insert comprising the radioactive material comprises a pod containing the radioactive material, wherein the pod is configured to move along a Z-axis of the measured insert as the imaging procedure occurs.

Clause 8. The in-scan phantom of clause 3, wherein the radioactive material is selected to represent an activity of a Standardized Uptake Value of approximately 1 in a nominal patient dose and weight.

Clause 9. The in-scan phantom of clause 3, further comprising a second measured insert comprising at least one of a low density foam, an ultra-low density foam, and an X-ray active gas.

Clause 10. The in-scan phantom of clause 3, further comprising a second measured insert comprised of a water-filled tube.

Clause 11. The in-scan phantom of clause 1, wherein the measuring insert includes radiation detecting properties.

Clause 12. The in-scan phantom of clause 11, wherein the measuring insert is configured to measure a total radiation incident on the insert during the imaging procedure.

Clause 13. The in-scan phantom of clause 11, wherein the measuring insert comprises a series of spatially-encoded radiation sensors spaced along a length of the insert.

Clause 14. The in-scan phantom of clause 1, wherein the measuring insert is capable of measuring at least one of patient motion during the imaging procedure, patient heart activity during the imaging procedure, radiation exposure during the imaging procedure, and patient weight.

Clause 15. The in-scan phantom of clause 1, wherein the phantom is in communication with a computer and the phantom is configured to transmit information collected by the measuring insert to the computer.

Clause 16. The in-scan phantom of clause 11, further comprising a measured insert.

Clause 17. The in-scan phantom of clause 16, wherein the measured insert comprises at least one of a low density foam, an ultra-low density foam, and an X-ray active gas an ultra-low density foam.

Clause 18. The in-scan phantom of clause 17, wherein the measured insert comprises an ultra-low density foam.

Clause 19. An in-scan phantom for use in an imaging procedure, the phantom comprising: a measured insert comprising a radioactive material.

Clause 20. The in-scan phantom of clause 19, wherein the measured insert comprising the radioactive material is configured to move along a Z-axis of the phantom as the imaging procedure occurs.

Clause 21. The in-scan phantom of clause 19, wherein the measured insert comprising the radioactive material is configured to be non-uniform along a Z-axis of the phantom.

Clause 22. The in-scan phantom of clause 19, further comprising a second measured insert comprising at least one of a low density foam, an ultra-low density foam, an X-ray active gas, and water.

Clause 23. The in-scan phantom of clause 22, further comprising a measuring insert.

Clause 24. The in-scan phantom of clause 23, wherein the measuring insert includes radiation detecting properties.

Clause 25. The in-scan phantom of clause 23, wherein the measuring insert is capable of measuring at least one of patient motion during the imaging procedure, patient heart activity during the imaging procedure, and patient weight.

Clause 26. The in-scan phantom of any of clauses 1-25 wherein at least one of the inserts is removable from the in-scan phantom.

Clause 27. The in-scan phantom of any of clauses 1-26 wherein at least one of the inserts is permanently affixed to or within the phantom.

Clause 28. An imaging modality system, comprising:
an imaging modality; and
the in-scan phantom according to any of clauses 1-27.

Clause 29. The imaging modality system of clause 28, wherein the imaging modality system is a combination imaging modality system selected from a PET/CT combined modality and a PET/MR combined modality.

Clause 30. The imaging modality system of clause 28, further comprising an auxiliary device system that receives information measured by a measuring insert of the in-scan phantom.

Clause 31. A method, comprising:
placing a patient within an imaging modality of an imaging modality system, wherein the imaging modality also contains the in-scan phantom according to any of clauses 1-27;
imaging the patient and the in-scan phantom using the imaging modality.

Clause 32. The method of clause 31, further comprising removing at least one insert from or inserting at least one insert into the in-scan phantom prior to imaging the patient and the in-scan phantom.

Clause 33. A method, comprising:
placing a patient within an imaging modality of an imaging modality system, wherein the imaging modality also contains the in-scan phantom according to any of clauses 1-27;
performing a scout scan using the imaging modality.

These and other features and characteristics of the contrast imaging agent, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE FIGURES

The Figures associated with the present disclosure describe specific embodiments and should not be considered limiting to the overall disclosure as set forth in the claims.

FIGS. 1A and 1B illustrate prior art imaging platforms from U.S. Pat. No. 4,233,507, the disclosure of which is incorporated herein by reference in its entirety.

FIG. 2 illustrates a cross-sectional view of one embodiment of an in-table phantom with multiple inserts according to the present disclosure.

DETAILED DESCRIPTION

Figure 3:
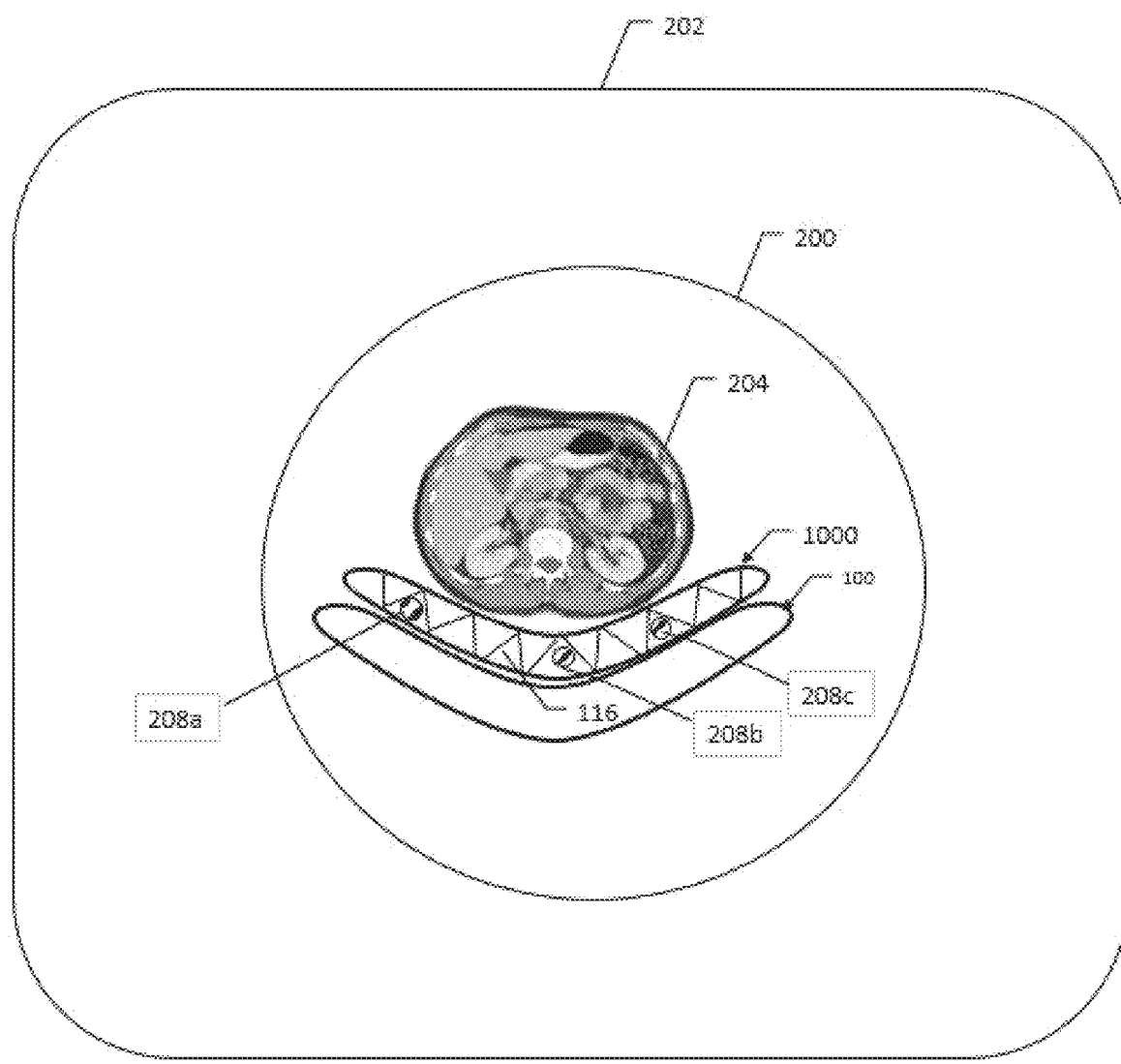
FIG. 3 illustrates a cross-sectional view of another embodiment of a phantom within the bore of an imaging modality according to the present disclosure.

The illustrations generally show preferred and non-limiting aspects of the present disclosure. While the descriptions present various aspects of the devices, systems, and/or methods described herein, it should not be interpreted in any way as limiting the disclosure. Furthermore, modifications, concepts, and applications of the disclosure's aspects are to be interpreted by those skilled in the art as being encompassed, but not limited to, the illustrations and descriptions provided herein.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

Further, for purposes of the description hereinafter, the terms "end", "upper", "lower", "right", "left", "vertical", "horizontal", "top", "bottom", "lateral", "longitudinal", and derivatives thereof shall relate to the disclosure as it is oriented in the figures. However, it is to be understood that the disclosure may assume various alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting. For the purpose of facilitating understanding of the disclosure, the accompanying drawings and description illustrate preferred aspects thereof, from which the disclosure, various aspects of its structures, construction and method of operation, and many advantages may be understood and appreciated.

Various embodiments of the present disclosure describe a phantom with materials selected to interact with an individual, multiple individual, or a combination of imaging modalities, e.g. PET/CT or PET/MR, for single or multiple procedures or protocols. The phantoms that are the subject of this disclosure provide flexibility and quantitative information gathering capabilities that were not available in phantoms previously known in the industry.

As used herein, the term "phantom" describes a physical structure that, when subject to an imaging procedure, provides additional information independent of the patient measurement that can be used to inform about, adjust, or interpret the imaging system and or measurements of the patient. As used herein, an "in-scan" phantom is a phantom that is present within the imaging modality during at least a portion of the time while the patient is being imaged and, accordingly, is imaged contemporaneously with, or nearly contemporaneously with, the patient. In-scan phantoms are usually sized and configured such that, as the imaging procedure captures images of the patient, a corresponding portion of the phantom is imaged at the same time. Thus, one or more image slices or volumes of the patient that are captured during the imaging procedure can also include a measurement or image of the insert. The phantoms described herein have greatest utility as in-scan phantoms, though in addition or alternatively, they can also be used to calibrate an imaging modality by scanning the phantom separate from the patient for quality control (QC) or calibration of the imager or the process.

The phantoms described herein may contain one or more "measured inserts," which are objects with properties, which may be the same or different in type or value, known in relation to the imaging modality and procedure being used. One or more of those properties are measured during the making of a measurement or creation of an image by the imaging system. A measured insert may be comprised of one or more imaging measuring compounds or materials. In this sense, the measured inserts can be used as a reference or references when performing an imaging procedure to aid in the image analysis. The phantom can contain at least one measured insert whose geometry and/or properties are selected and/or known to a sufficient accuracy and/or precision with respect to the imaging modality or modalities in use, for example through first principles, indirect measurements and calculation, direct measurement (including through the use of a dose calibrator), or in comparison to or with reference to a calibrated standard. Example properties that the one or more measured insert may have include but are not limited to atomic composition, concentration, and/or density for CT, proton density, T1 and T2 for MR, positron activity or radioactivity for PET, sound transmission speeds and interface reflectivity for ultrasound, among others. The phantoms described herein may also contain one or more "measuring inserts," which make a measurement or capture data about the imaging procedure. The measured or measuring inserts may be removable from the phantom or they may be permanently affixed to or within the phantom, or constitute a portion of the phantom body itself. A plurality of inserts having different properties may be used during specific imaging scanning modalities to provide qualitative and/or quantitative measurements for those properties.

The phantoms according to the various embodiments of this disclosure can be used in individual modality systems and combination image modality systems. As used herein an individual modality system is one that creates a patient image using only a single modality, such as a CT imager, a PET imager, a SPECT imager, an ultrasound imager, or an MR imager. As used herein, a combined or combination imaging modality system is one that uses two or more imaging modalities to create a single or composite image. The combined imagine modalities may be fused, either in the same imager, such as a PET/CT combined modality, produced simultaneously, for example as a PET/MR combined modality may do, or be done sequentially. For use in combined image modality systems, the phantom should incorporate at least one material which responds in a known way in each of the applicable imaging modalities and the protocol(s) selected.

The phantoms that are the subject of this disclosure assist in the collection of information about an imaging procedure. In particular, the information gained from imaging the phantoms described herein allows for better qualification and/or quantification of the imaging procedure and, moreover, are useful across different modalities, such as CT, PET, SPECT, MR, ultrasound, optical, photoacoustic, and other imaging modalities, and combinations thereof. The inclusion of inserts with known qualities and/or properties helps ensure consistency in the image analysis over time. Some of the benefits include: improving the consistency in the image analysis for a single patient, over time for the same imager, between imagers, and across different imaging protocols and/or reconstruction algorithms whether on the same or different imagers; helping facilitate transfer between imaging modalities; checking for co-registration of multiple modalities, for example PET & CT or MR; checking for patient motion; checking the accuracy of motion correction or compensation; verifying correct 3D reconstruction; checking for geometric and/or time distortion and/or resolution, modulation transfer function (MTF), and/or other image pattern, texture, or quality characteristics. Specifically in the case of CT imaging, the present phantoms can enable assessment and/or correction of beam energy spectrum choices and modification thereto such as beam hardening and the effects of the actual beam energy spectrum on imaging system measurements, whether a single energy or a dual energy system. The information from the phantoms may be used to inform image reconstruction in a variety of ways, examples of which are discussed herein. In embodiments with phantom elements at various positions, the radial, axial, and circumferential variation of properties discussed herein can also be assessed and/or adjusted. For PET it may be especially useful to assess and correct for attenuation correction inaccuracies. With a radioactive phantom element, cross correlation or quantification with an external standard or dose calibrator may be improved.

The various embodiments of the phantoms and combinations of phantoms referenced herein are not limited to a particular structure(s), and may take on various forms depending on the intended placement relative to the patient or imager. By way of example, and as will be explained in further detail herein, the phantom may be part of the imaging modality, such as part of the imaging table upon which the patient rests and therefore move as the patient table moves. Alternatively, one or more aspects of the phantom can be permanently located in the imaging volume of the imager and thus not move with the patient table. The phantom can also be part of a device that is placed within the imaging modality, such as an anti-roll pad, cushion, or pillow formed of foam, air, or water that is laid under, on top of, or next to a patient. The phantom may also be a structure designed to be placed beside the patient. The phantom may alternatively be part of a structure designed to be worn by, placed on, or affixed to the patient, such as a vest, blanket, or patient marker. The phantom may alternatively be affixed to the patient by adhesive, strap, or other means. Phantoms such as this may move or experience a force or stress with some movements of the patient and thus be used to assess patient motion. The position of the phantoms in relation to the patient and the imager may depend upon the body habitus of the patient and/or the study being conducted. In some non-limiting embodiments, the phantom may also be part of a surface coil (such as an MR surface coil) or in an ultrasound coupling pad. Moreover, a phantom can comprise distinct and separate structures, including various combinations of individual phantoms described herein, that, together, function to provide additional information about the patient measurement. By way of example, a phantom can include the combination of a wearable vest and a portion of the imaging table, each containing one or more inserts that collectively function to provide additional information about the imaging procedure. In some embodiments, the phantom can be configured to be removable if additional space is needed to accommodate a larger patient. In addition, to the extent the phantom includes radioactive materials, the phantom (or at least the radioactive portion thereof) can be configured to be quickly removed prior to performing a background scan or other procedure where a radioactive phantom is not needed. Radiation can also be limited by including a shielding element that moves in place (manually or automatically) to shield the patient or the imaging system from exposure from the radioactive insert when the radioactivity is not needed.

FIG. 2 illustrates the cross section of an embodiment of an imaging table 100 that can be utilized in the present disclosure. Imaging table 100 has spaces for one or more inserts, which in this embodiment form the phantom. The table has a top surface 110 to hold the patient and an optional bottom surface 112 for structural integrity and to interface the table with the support stand that holds and moves the table relative to the imager. The table may be configured to move in various directions, such as in and out of the imager and up and down to center the patient. The table has bridging material 114 that separates the top surface from the bottom surface and/or the table support. In this example, the bridging material 114 is relatively strong rigid material, for example a carbon fiber material, similar to the table top and bottom material. Alternatively, the bridging material may comprise rigid foam or other material. The material of the table 100 is generally not active to, or may be deleted from the image modality so that the table does not appear in the image. Similarly some or all of the images of the phantom may be deleted form the images presented to the doctor or patient although the data from the phantom may still be used as described herein by the imaging system. The bridging material 114 may form a honeycomb or web to further strengthen the Z-axis of the table 100. The phantom also includes openings, channels, or holes 116 for the insertion of one or more inserts. The holes 116 may be of different shapes, such as round, square, triangular, trapezoidal, hexagonal, etc. In certain embodiments, the table 100 may incorporate one or more inserts each of which may be either removable or permanently incorporated into table 100 to form the phantom. The inserts could be exchanged between patients or could be exchanged on a less frequent basis, such as once a week or once a day depending on the schedule of imaging procedures and required phantom properties. Use of inserts having the same or different phantom properties allows the technician to adjust the overall phantom properties as desired. Tables having other shapes/structures may also be used.

FIG. 3 illustrates the cross section of another embodiment of a phantom that can be used in the present disclosure. In this embodiment, phantom 1000 is a separate element from the imaging table 100 and is disposed within the bore 200 of the imaging modality 202 between the patient 204 and the imaging table 100. Phantom 1000 can be in the form of a pad that is placed on the imaging table 100 that the patient 204 can then lie upon. Phantom can include openings, channels, or holes 116 for inserts 208a-c, such as described herein.

Figure 4:
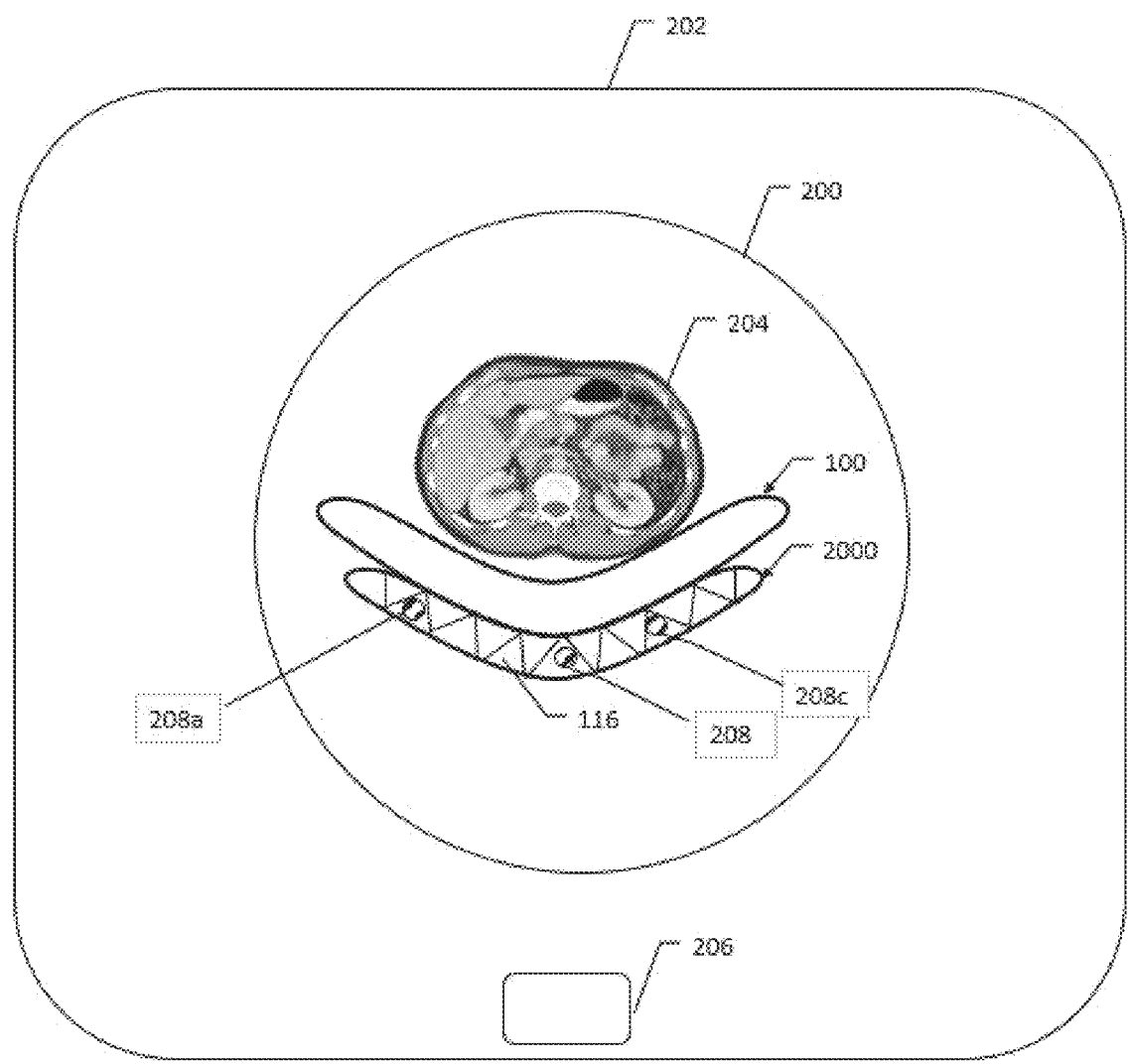
FIG. 4 illustrates a cross-sectional view of another embodiment of a phantom within the bore of an imaging modality according to the present disclosure.

FIG. 4 illustrates the cross section of another embodiment of a phantom that can be used in the present disclosure. In this embodiment, phantom 2000 is a separate element from the imaging table 100 and is disposed within the bore 200 of the imaging modality 202 underneath the imaging table 100. Phantom can include openings, channels, or holes 116 for inserts 208a-c, such as described herein. In this embodiment, the imaging table 100 may move axially in and out of the bore 200 with the patient 204 resting thereon while the phantom 2000 may stay within the bore 200 and not move axially with the patient 204 and imaging table 100. The imaging modality 202 can have an insert storage area 206 associated therewith for storing various inserts that are not in use for a given procedure, such as in the form of a retractable compartment embedded in the imaging modality.

According to these embodiments, the storage area 206 may be shielded from the imaging area to prevent unwanted image noise or exposure to radioactive material in the inserts. A benefit of this embodiment is that the inserts may be smaller and lighter. The inserts themselves need not be longer than the imager sensitive length which is much less than the length of the patient bed. In addition, an automatic or robotic mechanism similar to a tool changer used in automated computer numerical control (CNC) machine tools may be incorporated to automatically change inserts based upon the imaging procedure, thus simplifying the work of the operator or technician and reducing the chance for human error. In an embodiment where insert switch is performed manually, having the storage area 206 with defined places for each insert again simplifies the procedure and reduces the chance for human error.

The various embodiments described herein include phantoms having one or more "measured" inserts, phantoms having one or more "measuring" inserts, and phantoms having various combinations of both "measured" and "measuring" inserts. For purposes of this disclosure, a "measured" insert is one that is measured by the imager and provides a qualitative and/or quantitative reference point, or benchmark, that can be used when setting up for image acquisition, creating, reconstructing, and/or interpreting the image. A "measuring" insert is one that, in addition to or instead of being measured by the imaging system, also makes a measurement and/or captures data, such as a measurement related to the patient's heart activity (e.g., pulse or ECG), respiration, weight, brain activity (e.g., EEG), motion, or the level of radiation that the phantom (and thus the patient) is emitting or subjected to. Because of the data capture element, measuring inserts may include the necessary electronics and communication modules to allow the captured data to be stored and/or transferred (optionally in real time) to the appropriate location, such as an imager processor for processing during image construction or reconstruction. Alternatively, the necessary electronics may be part of the imaging system. The data from the measuring insert may be transmitted to the imager for use in measurement and image creation, image or imager QC, and/or may be sent to one or more additional systems, for example a dose recording and assessment system, and hospital information system (HIS) or a picture archiving system (PACS). Image data from the measuring insert may be transmitted by a wired or wireless system (such as blue tooth or WiFi) to the imager, image processor, or other system.

A measured insert may contain one or more reference materials each having properties and/or concentrations known in relation to the imaging modality and procedure being used, for example in the form of an image active compound or material that is used to form the insert. Measured inserts can be homogenous and extend uniformly and longitudinally along the length of, or laterally or obliquely across the phantom area. However, as described herein, measured inserts of the present disclosure are not limited to those that are homogenous and uniform, and some variation along their longitudinal or lateral length is possible and may be useful. As discussed herein, when used as part of an in-scan phantom, each slice of the patient that is captured during the imaging procedure may, depending on the location of the insert, also include a slice of one or more of the one or more inserts. The resulting image will display for example as a cross sectional slice or set of slides, a 3D rendering, an overlay of multiple images (optionally from multiple modalities), a time sequence or movie of images, or a motion removed image or series of images of the insert which can be used as a reference to make various determinations and computations related to the imaging procedure. For instance, the reference image or portions of the image can be used to ascertain the body composition of the patient by comparing the attenuation of the patient with the attenuation of the reference material of known composition in the insert and/or phantom. The reference image could also be used to assess noise and/or quality of the patient image relative to the insert/phantom reference material and, for example, determine whether a beam hardening or other correction algorithm should be employed. Additionally, based on any difference between the actual attenuation of the reference image from the insert/phantom and the expected attenuation, adjustments could be made during the image creation process, such as for iterative reconstruction. For example, the adjustment could include a correction in the Hounsfield Units after computation by shifting the histogram or adjusting or shifting the gray scale or color of the image to be displayed based on image data from the insert and/or phantom. The adjustment may include determining an effective beam energy or energy spectrum with which to associate the measured Hounsfield Units, a so called "Spectral Hounsfield Unit". The image of the measured insert or phantom can also be used to determine whether changes in the patient image over time are due to actual changes in the patient or if instead are the result of inconsistencies in the imaging procedure itself, for example as shown by changes in the insert image properties. According to various embodiments, the time frame of interest may be within a single imaging session, for example from a time sequence or series of images or as a physiologic process evolves, for example for pharmacokinetic—pharmacodynamics modeling of a heart beating, of lungs breathing, of peristalsis, and/or of elimination; or between subsequent imaging sessions, for example on different hours, days, weeks, months, or years. Since the composition of the reference materials in the one or more inserts is known, differences in the reference image of the one or more inserts that are observed across different imaging modalities, over time in the same modality for different patients, or over time in the same modality for the same patient, can be attributed to drifts or changes in the imaging modality itself or the modalities interaction with the patient as opposed to changes in the patient. Appropriate corrections can then be made either to the operation of the imaging modality or to the interpretation of the resulting image.

Selection of the various materials used to form the one or more measured inserts used in a particular phantom depends on a variety of factors, including the modality or modalities being used, the purpose of the imaging procedure (e.g., what is the target diagnosis), the region of interest of the scan, the patient size, the imager parameters, etc. Example properties that may be incorporated into the one or more inserts include but are not limited to atomic composition, concentration, and density for CT, proton density, T1 and T2 for MR, positron activity or radioactivity for PET, sound transmission speeds and interface reflectivity for ultrasound, and so on including combinations of two or more of these properties in a single insert.

Non-limiting examples of materials that can be used to form the inserts include known concentrations of calcium apatite, iodine (such as iodine in polymer, CT or MR contrast agent mixed with a suitable solvent such as water, tetraiodoethylene, cross-linked poly(vinyl pyrrolidone)-iodine complexes, and/or those materials referenced in U.S. Pat. No. 4,724,110 to Arnold, which is incorporated herein by reference in its entirety, uric acid crystals, water, tissue equivalent plastics (e.g., A-150 plastic developed by Shonka), polymers such as nylon, acrylates, polystyrene, or polypropylene, various blends or mixture of materials (e.g., a blend of nylon and uric acid crystals), and/or other materials of known utility in quantification phantoms, such as those described in United States Patent Application Publication No. 2014/0294140 to Kirby et al., which is expressly incorporated herein by reference in its entirety. In other embodiments, the inserts may also include one or more radioactive materials, such as long lived isotopes such as those useful for PET (e.g., Ge-68) or SPECT isotopes (e.g., Co-57). Other potentially useful radioactive materials include those manufactured and used in QC phantoms, for example those supplied by Eckert Zigler. In certain non-limiting embodiments, the radioactive insert may include a scattering material cylinder around an isotope material or a recombination material around a PET isotope insert. In general, inserts may be solids, liquids or gasses in a solid container, and combinations thereof, such as for example, gas containing solid spheres in a liquid. The solids may be moved and the fluids may flow as described herein. The phantom or an insert may include gas or liquid filled hollow spheres that move in a fluid, either a gas or liquid, such as happens with a Galileo thermometer. The motion may be active, for example motorized and controlled by the operator or the imager, or passive.

In certain embodiments utilizing a Dual Energy CT imager, for example, it may be possible through material decomposition software to measure the amount of one or more other materials either present in one or more tissue or organ of the patient, in one or more other inserts, and/or, for example, in one or more cold segments of a segmented radioactive insert. For example according to one embodiment, the amount of iodine in the blood can be determined relative to an insert and may be utilized to measure perfusion in the patient and can be assessed relatively independently of tissue density. An alternative embodiment, assessing the presence or absence of uric acid crystals and amount, when present in the patient, relative to a uric acid insert may be utilized in assessing gout in a patient. In still another embodiment, xenon concentration during xenon gas inhalation may be assessed and utilized in lung imaging. If a study is being done assessing one or more the above, it is desirable to have an insert which contains for example, known concentrations of iodine or iodine containing material, uric acid crystals and/or calcium containing crystals, or xenon gas, respectively.

By way of another example, in CT imaging of certain organs or tissues, such as the lung, very low density regions are measured. In an embodiment for this disclosure, the insert can be a thin walled tube of aluminum, carbon fiber material, or other CT-inactive material to provide structural integrity and rigidity that is filled with an ultralow-density foam with known, measured, or calibrated densities. Example foams are polyurethanes which can be 0.015 gm/cm$^3$ or the foams described in United States Application Publication No. 2014/0142207 to Singhal et al., the disclosure of which is hereby incorporated by reference in its entirety, which can go down to 0.005 gm/cm$^3$. The insert tubes may be open to the atmosphere or closed and filled with a known pressure of a known gas. The foams may be filled with air or in certain embodiments, gases that are active in an imaging procedure, such as xenon or krypton gas in a CT X-ray procedure. In other embodiments, the foam may be filled with a liquid, such as pure water, for MR, or a solution of water with one or more image active compounds, such as a CT or MR contrast agent at a known concentration. Alternatively, the thin walled tube could be filled with many tiny, hollow spheres, each with sufficiently thin walls to have the desired density. According to other embodiments, the hollow spheres may be filled with a gas or liquid, such as air, xenon, krypton, water etc., as described herein. Alternatively, one or more aspects of the phantom or the one or more inserts thereof may contain one or more perfluorocarbons or other gas evolving contrast materials as described in International Application PCT/US2016/018707, filed Feb. 19, 2016, the disclosure of which is incorporated in its entirety by this reference.

A phantom including a combination of one or more different types of measured inserts, such as ones comprised of different materials, the same materials at different concentrations, or having different sizes or shapes, can provide additional qualitative and/or quantitative information beyond what can be provided using a single type of measured insert, during single imaging modalities and particularly if multiple imaging modalities are being used for the imaging procedure. For example a first insert may contain material with known CT properties and unknown MR properties. This can be paired with a second insert of known MR properties but unknown CT properties. In certain embodiments, the first and/or second insert may have known CT and MR properties or the first and second inserts may have only CT and only MR properties, respectively. Alternatively a single insert, for example pure water or air can act with known properties in multiple modalities. In another example, a PET isotope insert may be made of materials based upon stability and usability related to the radioactive properties but is not necessarily standardized or useful with relation to CT. Thus a PET emitter containing insert may be paired with one or more CT standard inserts for a PET/CT phantom or one or more MR standard inserts for a PET/MR phantom.

For example, the phantom may include at least one insert having PET active materials, such as described herein. The same phantom may further comprise one or more inserts that may be a water filled tube, such as insert 120a in FIG. 2, which determines the 0 calibration value for the Hounsfield Unit (HU) scale for the CT procedure. For the PET imaging procedure the water filled insert may contain a known radioactive as described herein. An insert having pure water may also serve as at least a portion of a phantom useful for MR. The combination of the MR phantom and a PET phantom, or a phantom that contains inserts useful in both MR and PET, may provide for a combined modality imaging procedure. In this phantom, there are for example three water tubes 120a, 120b, and 120c at different positions on table 100 to assess any beam hardening, geometric distortion, noise, and/or other non-uniform effects during imaging. Alternatively in other embodiments, such as for a CT lung study, it may be desirable to have multiple ultralow-density foam inserts at multiple positions of the phantom as a uniformity check, since the HU of this material is in the imaging region of the HU scale that is most important diagnostically for imaging of lung respiration. Embodiments that include combinations of ultralow-density foam filled inserts with positron emitter inserts allow for combined PET/CT modalities. Examples of lung imaging studies are described in Quantification of Regional Ventilation—Perfusion Ratios with PET, Melo, et al.; J Nucl. Med. 2003; 44:1982-1991, which is expressly incorporated herein by reference. Alternatively in other embodiments, incorporating one or more inserts having X-ray active gases, such as xenon or krypton gas, optionally at different concentrations in different inserts, in combination with one or more insert including a positron emitter, may provide for combined PET/X-ray or PET/CT modalities.

According to certain embodiment of the present disclosure for use with PET, PET/CT, PET/MR imaging modalities, the phantom may include at least one insert that incorporates a long lived PET emitter, for example positron emitter Ge-68 ($T_{1/2}$=270.8 days), although other suitable positron emitters can also be used. Typically, positron emitters with long half-lives may be used to limit the need for changing or recalibrating the phantoms due to radioactive decay over short time periods. However, positron emitters with longer or shorter half-lives are also within the scope of the present disclosure. For example, rods containing Ge-68, which has a long half-life and decays into a positron emitter Ga-68, have been used as transmission source rods in PET imagers, for example those manufactured by Eckert Zeigler. These rods usually contain quantities of Ge-68 that generate a significant amount of positron radioactivity, for example up to 120 MBq or 3.24 mCi. The transmission source rods are used to take a set of transmission measurements and create an attenuation map to be used to adjust the subsequent PET scan for attenuation by the patient, essentially serving the function of the X-ray tube in a CT imager. These rods are considered a source of X-rays (gamma rays) used in creating the attenuation map and are not used to acquire information during the patient scan. For safety reasons, these rods have to be shielded when not in use to protect the patient and the hospital personnel from needless radiation exposure. In addition, they also need to be shielded or removed from the imaging system to not interfere with the PET patient imaging. In this invention, inserts with significantly lower concentrations of Ge-68 may be used as described herein.

According to various embodiment of the present disclosure, the radioactivity of an insert which serves as an imaging phantom for a PET or SPECT procedure may contain significantly less radioactivity than used in prior art transmission sources. In particular embodiments, the concentration of the positron emitter in the phantoms of the present disclosure is such that the radioactivity is low enough that shielding is not necessary. Table 1 illustrates one example calculation of the activity for a Ge-68 PET emitting rod suitable for use as an insert according to certain embodiments of the present disclosure.

TABLE 1

| | Column B | | | Formulas for column B calculations |
|---|---|---|---|---|
| 1 injected activity | 10 | mCi | 370 MBq | |
| 2 patient weight | 70 | kg | 70 kg | |
| 3 activity/gm | 0.00014 | mCi/gm | 0.00529 MBq/gm | = B1/B2/1000 |
| 4 | 0.14286 | µCi/gm | 5.28571 kBq/gm | = B3 * 1000 |
| 5 insert rod diameter | 1 | cm | 1 cm | |
| 6 rod area | 0.7854 | cm² | 0.7854 cm² | = PI * B5²/4 |
| 7 rod length | 200 | cm | 200 cm | |
| 8 rod volume | 157.08 | cm³ | 157.08 cm³ | = B6 * B7 |
| 9 rod weight | 157.08 | gm | 157.08 gm | = B8 |
| 10 target SUV | 1 | | 1 | |
| 11 insert activity | 0.02244 | mCi | 0.83028 MBq | = B9 * B3 |
| 12 | 22.4399 | µCi | 830.27 kBq | = B11 * 1000 |

Such a rod may be suitable to be inserted into a phantom for use in a combined PET/CT phantom. The insert may be selected to represent the activity of a Standardized Uptake Value ("SUV") of 1 in a nominal patient dose and weight. For example, if a patient receives an injected radioactivity dose 10 mCi or 370 MBq (Table 1, row 1) with a patient weight of 70 kg (row 2), the delivered average activity per gm of tissue is 0.143 µCi/gm or 5.3 kBq/gm (row 4). An SUV is defined as the tissue activity concentration in a region in kBq/gm divided by the total activity given divided by the total patient weight. In this example embodiment, the insert may be a round, uniform rod of diameter 1 cm (row 5). For a 2 meter long rod (row 7), the volume is 157 cm³ (row 8). Thus, to have the rod represent a region of interest with an SUV of 1, the activity concentration needs to be that computed in Table 1 for the patient (Table 1, rows 3 and 4). For this calculation, the total insert activity is 22 µCi or 830 kBq. This activity is approximately $1/450^{th}$ of the radiation dose given to the patient, so having an insert with this radioactivity in the image will neither significantly increase the radioactivity dose to the patient nor significantly affect the counting statistics. Further, the radioactivity associated with the phantom PET insert will not significantly affect the radioactivity exposure dose received by hospital workers in comparison to the dose that they already are receiving from being in close proximity with the patient. The total radioactivity may be further reduced by having only discrete segments of the insert contain radioactivity of the desired concentration or quantity. For example, for an insert that is a rod of 1 cm diameter, a length of 1 cm may have radioactive material and a length of 9 cm may have non-radioactive material, and then a length of 1 cm may be radioactive again, and so on. For PET imagers with a bed distance of at least 20 cm, this insert would provide at least 2 radioactive inserts in the active volume, although not in every reconstructed slice, at all times. Each of these or combinations of these embodiments provides significant safety advantages over those utilized in the prior art. Still, it may be desirable for equipment cleaning or servicing to provide the capability to put a shield over the insert or to remove the insert into a shielded container, when not being used in an imaging procedure. The radioactivity of the insert will be sufficient to allow use as a phantom to determine various qualitative and/or quantitative values during a PET or combined PET/CT or PET/MR imaging modality(ies).

The materials that form the inserts can, in various embodiments, be solids, liquids, or gases or various combinations or solutions thereof. As described herein, for specific embodiments the material may be a foam contained within a hollow container, such as a low density foam or an ultra-low density foam or alternatively, may be a gas or liquid suspended in a foam matrix. In other non-limiting embodiments, the image active material may be a low density fiber tangle, or a series of hollow spheres or beads container within a hollow container.

In various embodiments, the inserts may take on a variety of physical shapes as well. In one example, the insert is in the form of an elongated tube that is shaped to extend along or across at least a portion of the patient's body. The cross section of the tube is not limited and may be, for example, a square, triangle, rectangle, circle or oval. With reference to FIG. 2, inserts 122 and 128 have a round cross section while insert 140 is oval. Tubes of different sizes and/or lengths can also be used, including tubes having a diameter of 1 cm round, 0.5 cm round, or 0.5×1.0 cm oval. The inserts may take on other shapes as well with a variety of shapes of inserts being used for a particular phantom. For example in FIG. 2, insert 130 is formed of a plurality of two or more small round rods having the desired imaging properties adjacent to each other, and may optionally include an outer tube for support. In other embodiments, the insert 124 may be an assembly of small beads having the desired imaging properties held within a tube, which may or may not be individually resolvable by the modality under consideration. Alternatively in other embodiments, concentric tubes may be utilized for inserts, wherein each tube may contain a different image active compound or different concentrations of the same image active compound, or combinations thereof. The material used to form the walls of the tube of the various embodiments of the inserts can be the same as the material within the tube provided the material is sufficiently strong to provide the tube with the requisite structural integrity. Alternatively, the insert container walls could also be formed from, for example, carbon fiber, aluminum, or a thin plastic such as heat sealed polyethylene terephthalate or other suitable polymeric material.

Figure 5:
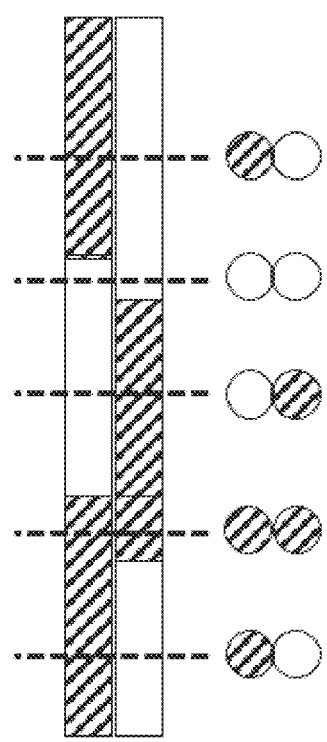
FIG. 5 illustrates a plan view of an insert illustrating the concept of Z-axis variation along the Z-axis of the insert.
Figure 6A:
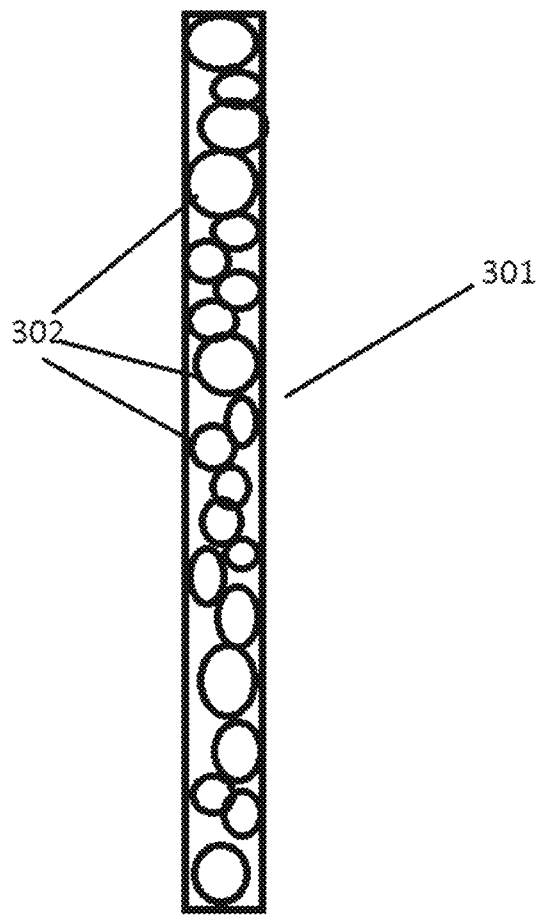
FIG. 6A-6F each illustrate a plan view of an embodiment of an insert for inclusion in a phantom according to the present disclosure.
Figure 6B:
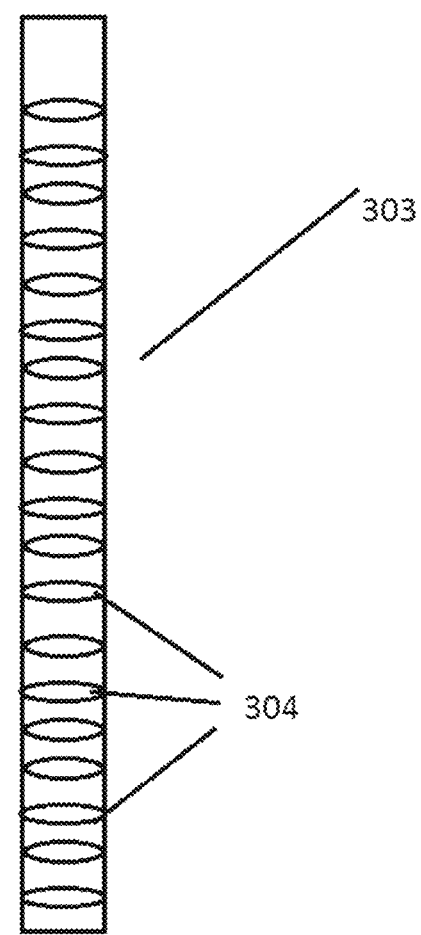

Variations in the shape, geometry, composition, concentration, and/or relative orientation of the insert along its longitudinal axis, which may also be referred to as the Z-axis, can provide additional information about the imaging process such as assessing the geometric accuracy of the patient position or assessing the uniformity of beam hardening. Thus, in certain embodiments, the shape, geometry, composition, concentration, and/or relative orientation of the insert may vary along its longitudinal axis as shown in FIG. 5 which illustrates a generalized phantom image that would be obtained at various points of the insert (each point represented by a dotted line) along the Z-axis. The pattern of Z-axis variations may be none, minimal, pseudorandom, random, periodic, pattern or information encoding (for example z-axis position), continuous, or discontinuous. There is no one right or optimum shape variation and the desired variation is dependent on the imaging procedure. Linear changes are most easily accomplished by an insert, or element of the insert, for example with a ramping or tapering profile. In one non-limiting embodiment, as illustrated in FIG. 6A, the insert 301 may be formed of a serious of balls 302 arranged generally in the Z-direction. The balls may be formed of the same or different compositions, may have different sizes and/or shapes, and may be interspersed with spaces or non-active balls or shapes. This configuration may be designed to provide variations in the insert, for example, in density, concentration, and/or radioactivity etc., along the Z-axis thereof. As illustrated in FIG. 6B, according to certain embodiments the insert 303 may alternatively be formed of a series of disks 304 aligned with one another along a common axis where the disks may have differing diameters and/or thicknesses. This configuration again provides variation in the insert along the Z-axis in an embodiment with the disks of a different material with different relevant imaging properties than the spacers.

Figure 6C:
Figure 6D:
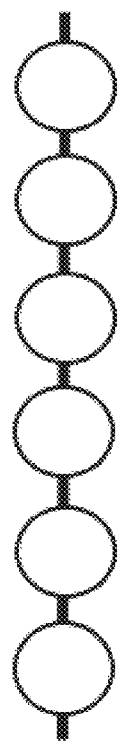
Figure 6E:
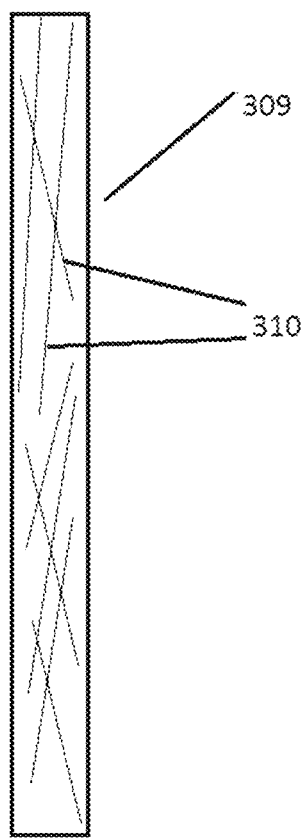
Figure 6F:
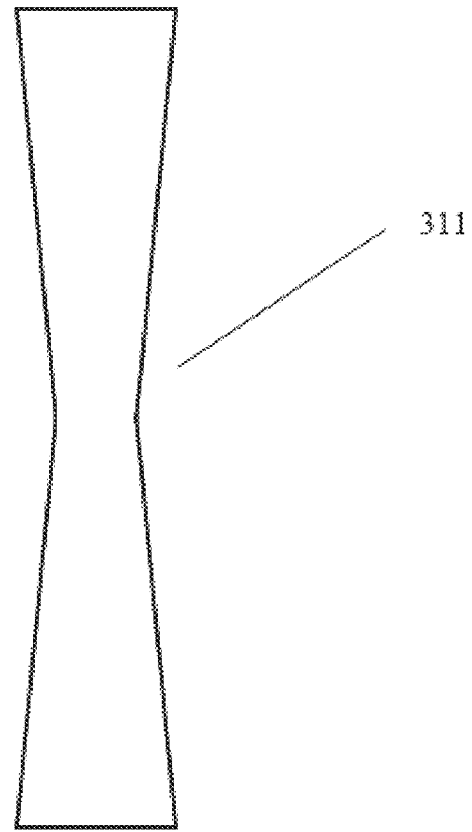

Other configurations that provide this effect are also envisioned according to certain embodiments, including an insert 305 that is spiral- or helical-shaped, as in FIG. 6C, an insert 307 formed of a series of spheres along a thin rod or line, as in FIG. 6D, or an insert 309 that is composed of thin rods 310 at different angles, as in FIG. 6E. By way of further example, the insert 311 may have a "dumbbell" shape wherein the diameter narrows near the middle of the insert, such as shown in FIG. 6F. The insert may alternatively be shaped like a step wedge or other shape with varying surface width/diameter, such as is shown in U.S. Pat. No. 5,841,835 to Aufrichtig et al., the entire contents of which are incorporated by reference. For example, two or more Z-axis varying inserts may be used to determine absolute Z-axis position within an imaging scan, for example the Z-axis material changes may represent a digitally encoded Z-axis position with the resolution thereof depending upon the number of inserts or other element used. The two or more Z-axis varying inserts may be of the same material or may be of different materials, so they may be used in different aspects of measurement assessment, for example attenuation correction or HU or radioactivity adjustment.

Depending on the modality being used with the phantom, other insert shapes/configurations/combinations may also be advantageous. For example, an insert having a larger CT shape with a smaller shaped PET inside the insert container or within the insert may have particular utility with a CT/PET combined modality systems. By way of another example, an insert useful with PET modalities may have a very small PET seed or sphere inside of a larger plastic tube or sphere such that the seed is effectively a point source for PET but of is still of such small quantities of material that it does not affect the CT imaging properties of the insert sphere or rod.

In certain embodiments, one or more inserts in a particular phantom may additionally contain an identifier that is "active" or "readable" by the imaging modality so as to allow the phantom to be readily identified and/or qualitatively and/or quantitatively measured through a review of an image thereof. For example, the phantom may contain a unique ID code in the form of a number, barcode, binary code, or other identifying indicia that is molded into or otherwise affixed to a portion of the phantom that can be read by the imaging modality. For example properly oriented letters can easily be readable by a CT scout scan by the user and/or by the imaging system. Another potential alternative is to create a bar code or digital code modification of the insert, for example by drilling holes through it or otherwise modifying the structure of the insert. Upon review of the image, the unique ID code would be visible, allowing the radiologist or technician, or imaging system to retrieve the properties of that particular insert(s) and/or phantom and use these properties in creating or interpreting the image. This retrieval process can also be automated whereby a computer system identifies the insert(s) and/or phantom and automatically retrieves information about that phantom from an associated database. Alternative ways of identifying the various inserts and/or resultant phantom are also envisioned, such as through the unique shape of the inserts or phantom or at least a portion thereof. In certain embodiments, some or all of the aspects of the insert(s) and/or phantom may be permanently associated with the imager, such that the identification can be done once by the system technician or operator and remain thereafter. Alternative identification methods may also be used.

In some non-limiting embodiments, one or more inserts in the phantom may be movable or contain a deployable component prior to, during, and/or after an imaging procedure. For example, a deployable feature may be particularly useful for an insert that contains a radioactive material, such as the PET inserts described herein, as it provides a way to limit the radioactivity exposure to the patient. In one embodiment, illustrated in FIG. 7, the phantom 400 includes an insert 405 containing a radioactive material where the longitudinal length of the insert 405 is significantly shorter than the length of the typical patient and also optionally shorter than the other inserts 410 within the phantom. In one example, the insert 405 is approximately as long as the region of interest, for example, the torso, head, etc., for the particular scan. Prior to the scan, the insert 405 is deployed, either manually or automatically, into position so that it coincides only with the region of interest. Because the insert 405 is shorter in length, it can contain a smaller amount of radioactive material as compared to a full length insert, thus limiting the overall exposure of the radioactive material to the patient. In certain embodiments, an even shorter insert can be used if it is capable of moving during the scan. For example, the phantom can include at least one insert, such as the shorter insert 405 discussed above, that moves in the Z-direction at approximately the same pace as the imaging beam moves in this same direction, thus effectively keeping the insert in the same position with respect to the imager as the scan proceeds. In this way, at any given point in the scan, the radioactive insert is generally in line with the portion of the body being imaged. However, the insert is generally not in line with portions of the body not being imaged at a given time, thus reducing the radioactivity exposure of those portions of the body. According to certain embodiments, movement of the insert can be done manually or through a motor element that can receive control commands from a computer or technician that is also in communication with the imaging modality. Other embodiments that achieve this same general effect are also possible. For example, with reference to FIG. 8, the insert 407 itself could be comprised of a long, hollow tube with a moveable pod 409 containing a radioactive material within. The pod 409 could move within the insert 407 in the Z-direction approximately in sequence with the progression of the scan in that same direction. An alternative way of achieving a similar effect includes (alone or in combination with the above) moving the patient relative to the stationary phantom (or portion of the phantom) having the required radioactivity as the scan progresses. Yet another alternative embodiment includes an insert filled with a medium that can receive an injection of radioactive material into the insert, where the flow or diffusion rate of the radioactive material through the medium from one point of the insert to another is similar to the rate at which the scan progresses. A similar effect could also be achieved by flowing bubbles or hollow spheres through an insert tube filled with a radioactive material. A movable insert is not limited to one that includes a radioactive material. These various methods may also be used with CT, MR or other contrast agents. Controlled motion of the insert can also be used to assess, measure, quantify, qualify and/or verify dynamics of the scan, motion blurring, or measure the speed and/or distance of the scan. Movement of the insert is also not limited to the Z-direction as rotatable inserts, such as one having a non-circularly symmetric (e.g., barber pole or automotive suspension coil springs) or static vane mixer configuration, are also useful. The insert may move in the X-plane, Y-plane, or a more complicated orbit or 2- or 3-dimensional pattern. One potential use of the information from movable phantoms is to assess motion blurring of the imaging system. For example, placing a small spherical phantom element or insert with a diameter of 1 cm and an SUV of 1 onto the chest of a patient can assess both the attenuation correction and motion blurring that occurs during a lung cancer imaging examination. If the imaging process employs motion correction, for example using a respiration monitor, the resulting image (for example as shown by sharpness, total SUV, etc.) of the phantom imaging element will be an indication the goodness, accuracy, or quality of the motion correction algorithm. It may also indicate if the motion correction algorithm introduces any artifacts or inaccuracies into the measurement or image. Alternatively, the motion correction algorithm, especially when using iterative reconstruction, could iteratively operate to maximize the sharpness of the phantom element. In an alternative embodiment, an insert with a 1 SUV point source (for example a small sphere) may be rotated in an orbit of several cm diameter so that over the PET acquisition time, it has moved through at least one cycle and optionally several cycles. This can be used to assess the motion blur of the system or image reconstruction algorithm.

The phantom may include, alone or in combination with one or more measured inserts, one or more measuring inserts, as described herein. Measuring inserts may also contain a reference material having known properties and provide much the same benefits as the measured inserts described above in addition to the measuring aspects. In addition, measuring inserts of the present disclosure provide additional information gathering capabilities in that they can be used to actively make a measurement of the patient or the imaging system.

One non-limiting example of a measuring insert is one that includes radiation detecting properties. This insert can be used during a scan to measure and track the actual radiation dose to which the patient is subjected. The insert can take on various physical forms, such as part of the phantom, part of a wearable vest or blanket placed on the patient, or any of the other physical forms described herein. In one embodiment, the radiation detecting measuring insert is a long, uniform tube, such as one similar in shape to insert 410 in FIGS. 7-8, for example acting as an ion chamber, extending along the Z-direction that measures the total radiation incident on the tube for the entire scan procedure. In one embodiment, this insert may be filled with a known gas, for example air at standard pressure and temperature (STP) and so serve as a measured insert relative to its contents as well. In another non-limiting embodiment, the radiation detecting insert includes a series of spatially discrete sensors spaced along the Z-direction of the insert. This embodiment provides the added benefit of allowing a slice-by-slice (or at least region-by-region) determination of the incident radiation. Other embodiments include ion chambers, scintillators and fibers, solid state diodes, other electronic radiation detectors, and combinations of any of the above. In another non-limiting embodiment, the radiation measuring detector may be a 2D or 3D arrangement or array of sensors, for example over the surface of the patient bed or in a blanket that is wrapped around the patient. Optionally, the actual position of the sensors is or can be assessed from the imaging scan sequence. Data collected by the insert may in real time or subsequently be transmitted to a computer where it can be stored and analyzed for example, during image deconvolution. This information can be used, for example, to ascertain the actual amount of radiation received by the patient and/or certain areas of the patient's body, to measure scatter, and/or to assess beam hardening for image creation. In certain embodiments, information about the actual radiation received by the patient can be compared to the expected/predicted amount of radiation exposure to test the accuracy of the prediction algorithm and to help develop more accurate protocols going forward. In addition, information about the radiation received by the patient can be added to the patient's file to guide future imaging procedures for that patient and help ensure the patient is not over-radiated. The data may be added for example to the associated DICOM image. For example, this information could be fed into a system like is disclosed in United States Patent Application Publication No. 2012/0150505 to Couch et al., which is expressly incorporated herein by reference in its entirety. This radiation dose estimation system may, for example, use the scan location as determined from the scout scan and the dose length product as output by the imaging system to assess various patient body geometrical and other characteristics, to compute the radiation dose to various organs, and thus to compute an effective radiation dose to the patient. Having actual measurements over time from a dose measuring insert or a 1, 2, or 3D array of measuring inserts would provide significantly more data than the radiation dose estimation software currently has to work with. For example, CT often uses tube current modulation to reduce radiation dose. Thus, the tube current changes as the tube rotates and as the patient moves through the imager. However, because the dose length product is summed over the whole scan, its variation with patient and tube position may be estimated. With independent radiation dose measurement data taking during the scan, the software can use this additional data to make a more accurate angular and positional dependent estimate of radiation field and thus a more accurate effective dose estimate may be made. In one embodiment, data about the amount of radiation dose received by the patient at a particularly point in the scan, as measured by the radiation detecting insert, can be compared to the expected amount for that portion of the scan in real time to allow the imaging protocol and/or operating conditions of the imager to be corrected on-the-fly. Optionally, one or more measuring insert(s) may be placed out of the imaging volume and thus not receive direct but only scattered radiation. The place(s) may be at a fixed and/or know location with respect to the imaging volume.

Other types of measuring inserts can also be used. For example, measuring inserts that measure motion of the patient or certain body parts or tissue during the imaging procedure may be incorporated into the phantom. This information could be used to ascertain whether irregularities in the image are caused by patient motion. By way of another example, measuring inserts that measure heart activity (pulse, ECG) can be used. These inserts can collect information about the patient's heart during the imaging procedure. This information can be used to, for instance, control the image acquisition by only allowing imaging during a certain phase of the cardiac cycle. These inserts could also be used retrospectively to put images into "bins" to allow the creation of a composite movie of, for example, the heart motion created over many distinct cardiac cycles. By way of yet another example, inserts that measure a patient's weight can be used to determine weight-based contrast dose or to adjust imaging parameters if, for example, the weight measured by the insert differs from the weight used to determine the parameters in the first instance (such as if a previous protocol is being repeated and the patient's weight has changed in the interim or for example if the operator enters an inaccurate weight for the patient).

Figure 7:
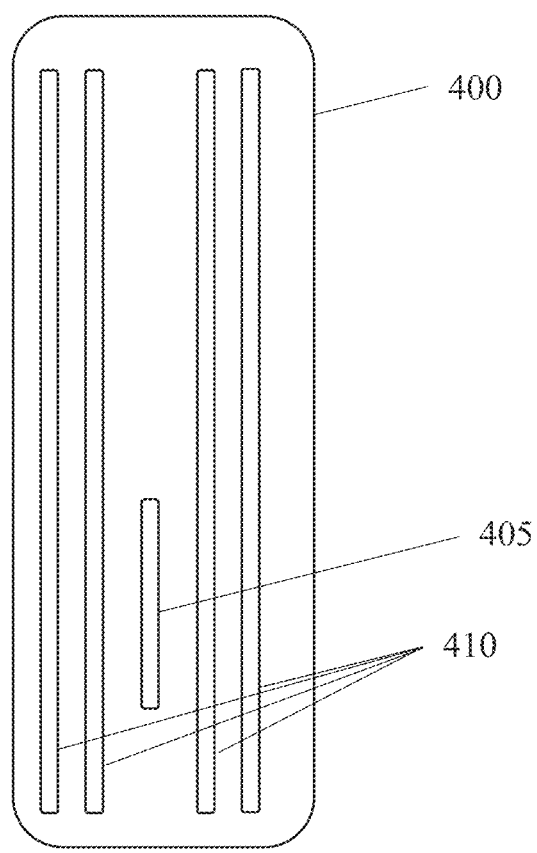
FIG. 7 illustrates a plan view of an embodiment of a phantom with a radioactive insert according to the present disclosure.
Figure 8:
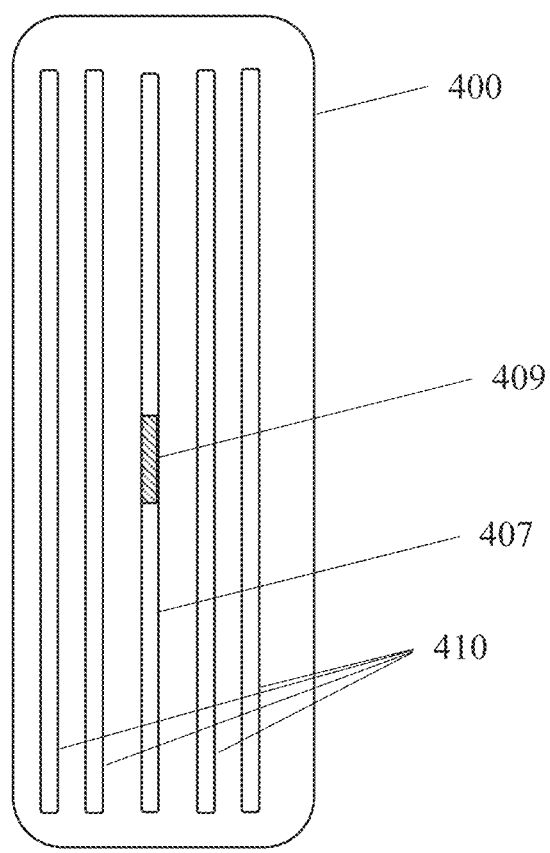
FIG. 8 illustrates a plan view of an embodiment of a phantom with an insert containing a deployable radioactive pod according to the present disclosure.
Figure 9:
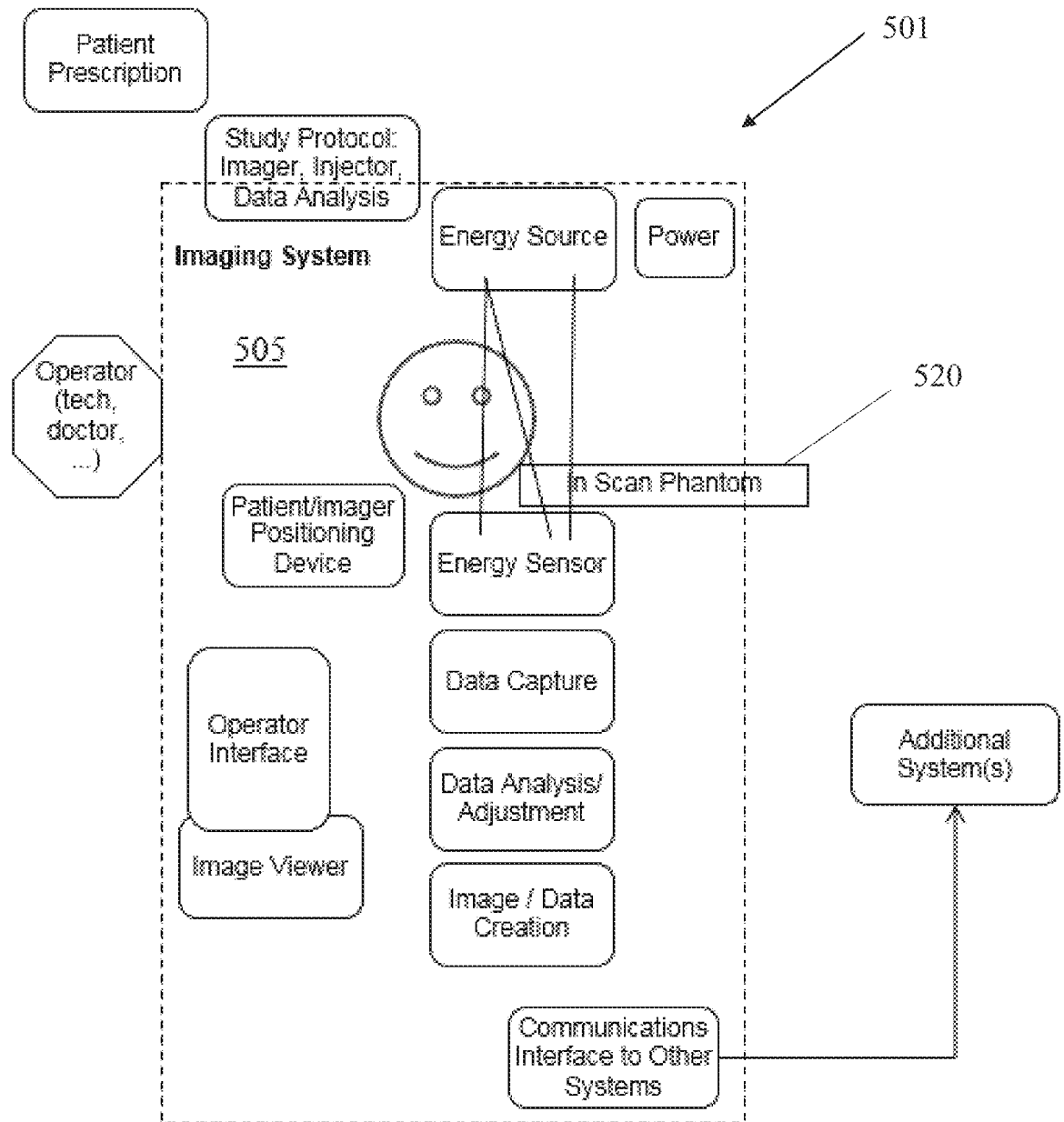
FIG. 9 illustrates a system diagram of one embodiment of a system in which the phantoms of the present disclosure can be used.
Figure 10:
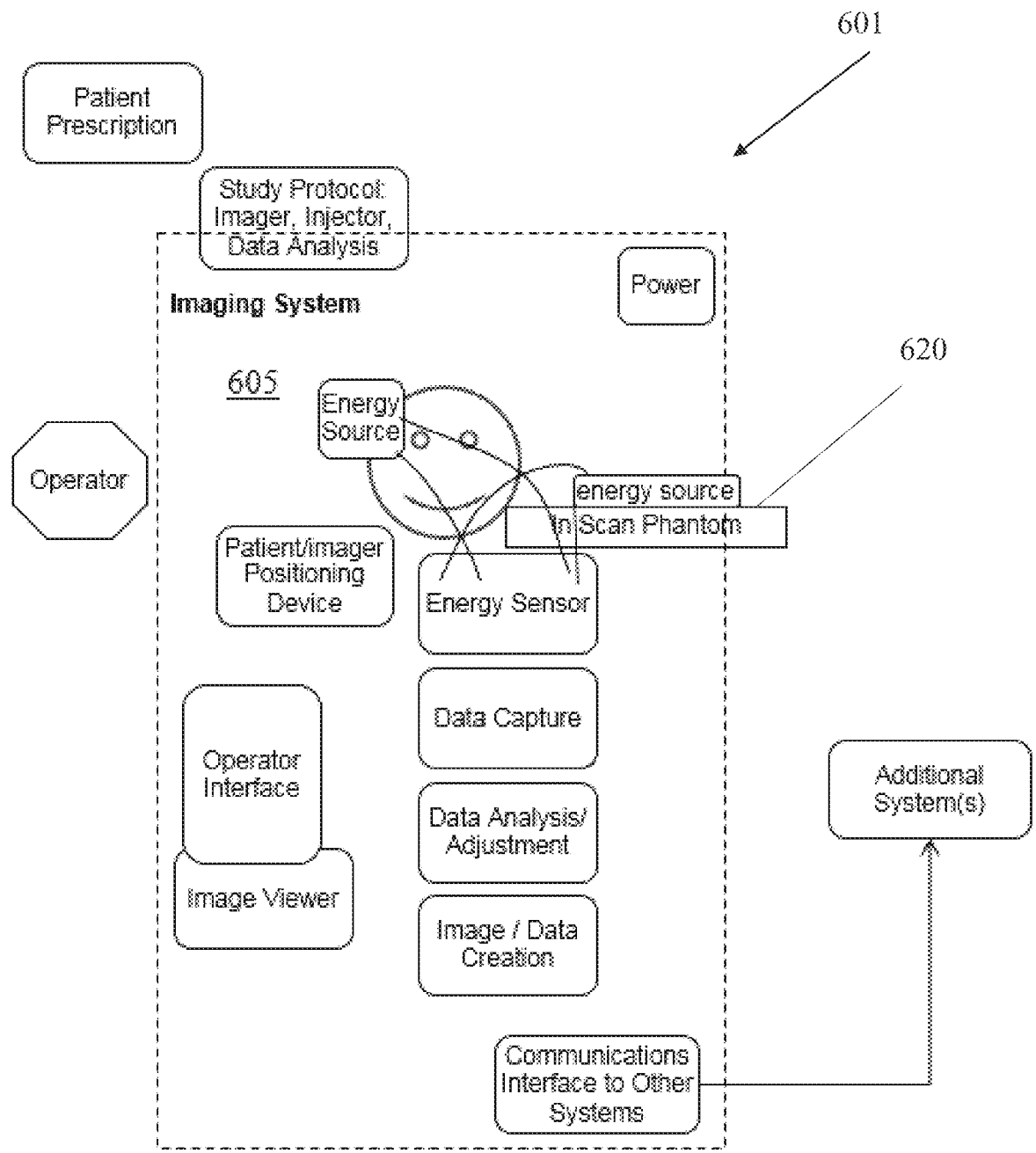
FIG. 10 illustrates a system diagram of another embodiment of a system in which the phantoms of the present disclosure can be used.
Figure 11:
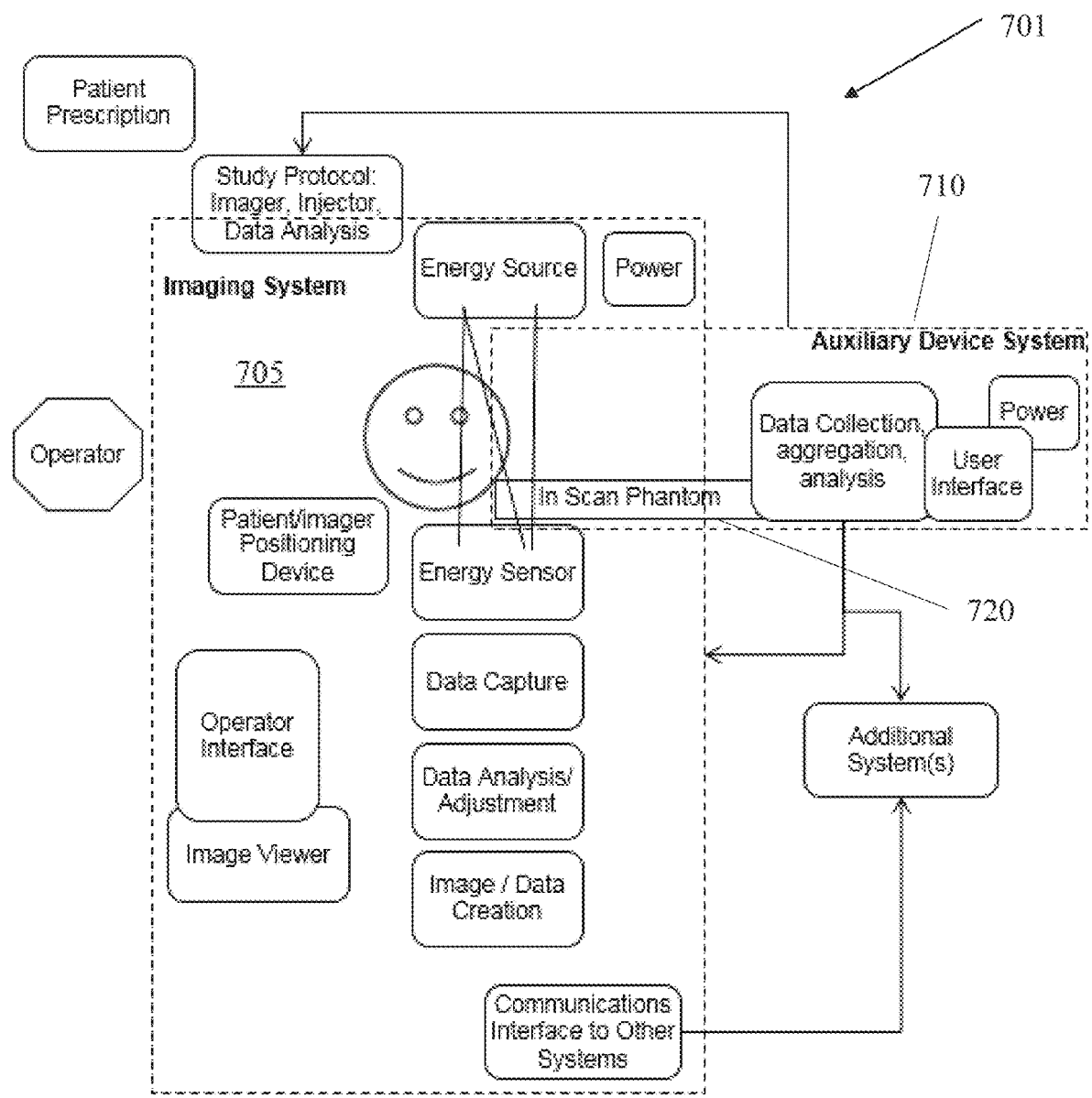
FIG. 11 illustrates a system diagram of another embodiment of a system in which the phantoms of the present disclosure can be used.

FIGS. 9-11 illustrate non-limiting embodiments of systems in which the in-scan phantoms described herein can be used. It should be understood that the systems in FIGS. 7-9 are not mutually exclusive or limiting, and elements from any one system can be combined with any other.

FIG. 9 illustrates one embodiment of a system 501 in which an in-scan phantom 520 including one or more measured inserts can be used to collect information about the imaging procedure. The system includes an imaging modality system 505 that images the patient through traditional imaging techniques using known modalities, for example CT, MR, or PET imagers commercially available from GE, Toshiba, Hitachi, and others. Images of the phantom 520, including the one or more incorporated inserts as described herein, are captured and displayed so that the operator or imaging system can adjust the imaging parameters as necessary. According to certain embodiments, phantom images can also be used for ongoing or periodic quality control, to assess noise and image quality, to adjust the Hounsfield Unit in the data analysis step, and/or to inform the image creation process, such as by using the phantom or various insert properties to adjust the kernel or number of iterations during reconstruction.

FIG. 10 illustrates another embodiment of a system 601 in which an in-scan phantom 620 including one or more measured inserts containing an emissive element, such as one or more PET emitter in a rod or other insert as described herein, is used. The system is similar to that shown in FIG. 7, though in this embodiment the in-scan phantom itself is an energy source.

FIG. 11 illustrates another embodiment of a system 701 in which an in-scan phantom 720 including one or more measuring inserts, and potentially one or more measured inserts, is used. The system 701 includes an imaging system 705 that images the patient through traditional imaging techniques using known imagers, such as CT, MR, or PET imagers commercially available from GE, Toshiba, Hitachi, and others. The system 701 can further include an auxiliary device system 710 that collects, aggregates, and analyzes other information about the imaging procedure, including information collected by the measuring insert(s) in the in-scan phantom 720 (or other auxiliary device). The auxiliary device system 710 can include, for example, a user interface, a processor with image analysis software, and a power source. The auxiliary device system 710 can communicate with the imaging system 705 and provide data that can be used in creating and/or adjusting the image/data output by the imaging system 705. Alternatively or additionally, the auxiliary device system 710 can communicate with a study review system 730. Data from the auxiliary device system 710 can be used, for example, to inform or automatically affect the study protocol, such as by adjusting the injector contrast delivery, imager kV, etc., before the image is created. Data from the auxiliary device system can also be transmitted to one or more additional systems. By way of example, radiation measurements made by an measuring insert can be communicated to a system like is described in United States Patent Application Publication No., 2012/0150505 to Couch et al., incorporated herein by reference, where it can be used to correct measurements for that patient and/or improve the system and algorithm for patient dose measurement.

As mentioned elsewhere herein, in-scan phantoms are seldom used because, for example, their use involves extra work on the part of the technicians to move them in and out of the imager. In addition, conventional inserts can increase radiation dose to the patient by having additional absorbing materials in the scan. Further, for many procedures, the level of quantification, precision, accuracy, and repeatability that phantoms can provide are not needed.

Embodiments described herein can mitigate the radiation dose increase. For example, a minimum dimension phantom, such as a phantom including 0.5 cm or 0.2 cm diameter elements for most of the phantom, can be used. In some embodiments, a 1 cm diameter segment or element may be inserted at various z-axis positions to allow for other assessments, for example noise statistics. Another alternative is to include elements that are continuous in the Z-axis, to lessen the amount of absorbing material and to allow for the material to appear with sufficient frequency in the scans. In an alternative embodiment, at least some and, in some cases, as much as possible, of the scanning is done with the X-ray tube or other radiation source on the phantom or insert side so that the radiation is absorbed first by the phantom/insert.

Also described is a method of using the phantoms and various imager inserts. For in-scan phantoms, the method can include placing the phantom within the imaging modality with the patient and scanning the patient and phantom using the imaging modality. In some non-limiting embodiments, the in-scan phantom is already present in the imaging modality at the time the patient is placed therein, such as in the case when the phantom is part of the imaging modality. In other non-limiting embodiments, such as where the phantom is removable from the imaging modality, the patient and phantom may be placed in the imaging modality at the same or approximately the same time. Because the in-scan phantoms that are described in this disclosure may be configured such that the inserts are removable and/or replaceable to allow the phantom to be tailored to each examination type and/or patient, the method may also include removing and/or inserting one or more inserts having the same or different imaging properties into the phantom in advance of the imaging procedure. For example, inserts housed in a compartment of the imaging modality may be removed from the compartment and placed in the phantom. In some non-limiting embodiments, the patient is imaged such that radiation approaches the patient from the phantom side or through the phantom, that is the back (assuming the phantom is underneath the patient and the patient is lying on their back) so that the phantom is positioned between the beam source and the patient, as radiation absorbed by the phantom will cause a reduction in the amount of radiation that reaches the patient. Since a CT scan requires at most 180 degrees plus the beam angle, this can measurably reduce the dose to the patient if this direction is preferred over the direction where the beam first penetrates the patient and then the phantom. One or more properties of the phantom and the patient are collected during the imaging procedure. This can include properties of the measured insert(s) measured by the imager as well as properties measured by the phantom through one or more measuring inserts. Information gathered about the phantom or by the phantom can be used when interpreting the images that result from the imaging procedure, as well as for other purposes, such as ascertaining the accuracy of the imaging protocol or the operating conditions of the imaging modality, adjusting the image parameters on-the-fly or for future procedures, and/or determining the radiation dose received by the patient. The in-scan phantoms of this disclosure can also be used during a scout scan. Use of the phantoms of this disclosure as part of the scout scan can help with patient alignment to ensure that analysis can be done correctly.

Data or information from the measuring phantom inserts and/or data and information about the measured inserts from the imaging system can be used before, during, and/or after an imaging scan or series of scans. For instance, before the actual image or data measurement acquisition, some type or preliminary measurement or assessment is often done. For CT, for example, a scout scan is commonly performed to confirm correct patient positioning and designate the region of the body/table to be scanned. An in-scan phantom of this disclosure may be used to provide information about system operation based, for example, upon the attenuation of a known insert, especially those not underneath the patient. It may also be used to assess the X-ray tube function if, for example, the measured insert includes a radiation measuring insert. In addition, an in-scan phantom may be used to assess patient breathing, heart rate, and/or motion for use in setting or adjusting scan or injection protocols. Further, during the scout scan, the presence and correct geometric relationship of the in-scan phantom insert(s) with the patient may be confirmed. This information can be particularly useful if the insert has radiation detecting capabilities because the insert's position relative to the patient will affect how the data collected by the insert relates to the effective dose the patient absorbs. An additional use of the measuring insert information may be to alert the operator or image system to an inappropriate condition, for example a patient who is too big or heavy for a planned protocol.

In MR, for example, a tuning sequence may be done when a patient is first inserted into the imager. During the tuning sequence, for example, an insert may be used to measure Specific Absorption Rate (SAR) to confirm correct operation. In addition, as is described elsewhere, the measurement of measured insert(s) may be compared to their known values, the correct geometric relationship between the patient and the in-scan phantom may be confirmed, and/or the relevant measurements may be made to provide input to scan or injection parameters.

By way of another example, before the actual PET scan in a PET/CT imaging procedure, the CT imager may be used to compute an attenuation correction map for PET using an in-scan phantom of this disclosure. This can be done in addition to the CT setup uses mentioned herein. This attenuation map effectively is a low resolution CT image, and thus the confirmations and adjustment described herein, including to the Hounsfield Units, may be applied to this process before the subsequent PET scan. In PET, a radiation detecting measuring insert may be used to confirm that the patient received the proper radiotracer dose so as to avoid a needless a CT. Other single and combination imaging modalities may employ similar or different preparatory measurement sequences, as would be appreciated by one of skill in the art upon reading the present disclosure.

By way of further example, a phantom containing measuring insert(s) like those described herein can be utilized during the scan, such as to monitor the ongoing imaging sequence by, for example, measuring radiation, SAR, and/or patient motion. In some embodiments, this information, such as a dose versus tube angular position and/or noise in a segment of a sinogram, may be transmitted to the imager control system and may be used by the imager control to automatically adjust the image acquisition process or protocol during the acquisition. Alternatively, the information collected by the measuring insert(s) may be displayed to the user through a user interface, providing the user with the information needed to take action, or at least to take note of a condition that exists during the imaging acquisition.

After the scan or between successive scans, such as with different sequences or bed positions, the data or information from both measured and measuring inserts may be used in other ways as well. For example, in CT the "as acquired" or measured Hounsfield Units (HU) for measured inserts may be compared to the known HU value for those inserts, with the difference being used to estimate or assess the energy spectra of the measuring radiation and/or to adjust the measured HU to a calibrated, adjusted or actual HU for use in the image creation and subsequent quantification or comparison. A correction algorithm may applied to this information in a variety of ways as would be known to one of skill in the art upon reading the present disclosure. Among the types of algorithms are linear, stepwise linear, or spline transfer functions. An exemplary benefit of including multiple measured inserts of different materials in the phantom is that information can be gathered from the phantom that would allow the estimation of both the effective spectrum of the beam and the HU correction. The information collected from the phantom may also be used to shift the gray scale/color of the image being displayed. In addition, the information may be used to identify and correct for beam hardening effects. The information may also be used as part of an iterative reconstruction algorithm, a sophisticated version of which would include information about the angular radiation fluence, noise, and may include a computation of the effective energy spectrum vs. angle and/or position.

Information about patient motion can also be collected through the use of the phantoms described herein. For instance, one or more geometrically fixed inserts may be used by the imaging system to detect patient motion. A measuring insert may also provide an active indication of a shift or motion of a patient. Alternatively, a measured insert that moves with the patient may provide a consistent point of reference that may be used by the image generation algorithm to compensate or correct voxel (image volume elements) position for patient motion such as respiration or head movement.

One or more rotating, translating, or otherwise moving inserts, such as those described herein, may be used by the imaging system as, for example, a mechanical clock to timestamp individual images in a sequence, to confirm the timing of the imaging system, to compare to the reconstructed image sequence timeline, to assess speed or timing related blurring, and to assess motion related effects on quantification of the imaging system. The movement of the insert may be motorized with the speed and geometric details of the movement controlled by the operator or under the control of the imaging system. For example, the insert can move along a track or channel that is within or on the phantom. The insert may be moved manually by the operator, for example in ultrasound imaging. The motion of the insert may be in relation to the patient, the imaging system, or both.

Yet another use of the data or information from the in-scan phantom is to inform the operator of the measured, calibrated, or actual properties of the one or more phantom inserts. For example, the numerical values for HU or the composition of the insert may be printed on or near the appropriate inserts in the created image. This can allow the technician or doctor to assess the accuracy of the image. This information may also be used by the imaging system or a physicist or hospital QC system as part of ongoing QC and imager adjustment or preventative maintenance procedures. Having an insert in the scan can help indicate patient motion or blurring as compared to other causes of blurring if, for example, the image of the insert is or is not blurred or noisy as well. Alternatively, the quality of the reconstruction of an on-patient insert can be used to give an indication of the quality of a motion correction algorithm, for example a correction for respiration. Also after the scan, the position of a measuring insert, for example a radiation or SAR measuring insert, may be confirmed and recorded for subsequent use by a dose calculation or estimation software.

To further illustrate the utility and advantages of the phantoms described herein, the following examples are provided.

CT Lung Density:

CT assessment of lung disease is one area that can benefit from the use of the in-scan phantoms discussed herein. The Hounsfield Unit scale is referred to as a linear transformation of the original linear attenuation coefficient measurement into one in which the radiodensity of distilled water at standard pressure and temperature (STP) is defined as zero Hounsfield units (HU), while the radiodensity of air at STP is defined as −1000 HU. In a voxel with average linear attenuation coefficient, the corresponding HU value is therefore given by:

$$HU = 1000 \times \frac{\mu - \mu_{water}}{\mu_{water} - \mu_{air}}$$

Where $\mu_{water}$ and $\mu_{air}$ are respectively the linear attenuation coefficients of water and air.

Normal lung imaging involves HU values in the range of −850 to −950 HU for air containing tissue. This is a relatively small range and the calibration points for the scale are water at 0 HU and air (at STP) at −1000 HU. Particularly for assessing patient response to treatment, it may be beneficial to have the CT images include in scan phantom inserts in this range, for example low and ultra-low density foams. This would provide one or more calibration points much closer to the HU region of use than water can provide. Inserts may be made closed or sealed having a fixed amount of gas, (for example 1 atmosphere at STP) or open so that the gas density that they contain depends upon ambient conditions. A benefit of the use of an ambient condition insert may be that the insert will reflect the air pressure in the patient's lung, and thus differences or adjustments between subsequent patient scans with the same insert will only represent changes in patient tissue, not changes in air pressure. In addition, if gas enhanced contrast and/or dual energy lung CT is being performed as discussed in International Application PCT/US2016/018707, filed Feb. 19, 2016, sealed inserts with gasses such as xenon or bromoperfluorocarbons, with or without foam may be used.

CTA-CT Angiography:

In CT angiography, especially of the heart, there may be several benefits to using measured inserts as well as measuring inserts. Measuring inserts may be used to assess cardiac cycle for the reconstruction of cyclical movies. Patient motion inserts may be useful to indicate excessive patient movement.

Measured inserts with varying concentrations of iodine in water may be used to correct or adjust estimates of the concentration of iodine in the vessels. This can be useful when measuring flow or perfusion via a sequence of images. It may also be useful when assessing the partial volume effect in small vessels. An additional insert or inserts with various concentrations of calcium may be useful when characterizing the calcium deposits that sometimes occur in artery walls. With a single energy CT, sometimes the iodine opacification or HU can be similar to that of calcium, causing erroneous interpretations. The concentration at which this occurs will depend upon the beam energy selected. By having two or more inserts with the different materials, the operator or imaging assessment program can indicate if an erroneous interpretation might have occurred and alert the operator or doctor. In an alternative embodiment, dual energy CT may be used to help differentiate calcium from iodine. In this embodiment, if measured inserts containing known amounts of iodine and calcium or a single insert with a known amount of both calcium and iodine are present, the material decomposition algorithm/software may be adjusted as has been discussed herein with reference to Hounsfield units.

CT Kidney Stone without Dual Energy:

In treating kidney stones, it is desirable to differentiate uric acid from non-uric acid kidney stones because the preferred treatment is different. Current single energy CT differentiation has some success, but is not good enough to be used commonly, as discussed in "Noninvasive Differentiation of Uric Acid versus Non-Uric Acid Kidney Stones Using Dual-Energy CT," Primak, et al, Acad Radiol. 2007 December; 14(12): 1441-1447, which is incorporated by reference. A contributor to this overlap in HUs between the two stone types may be the various sources of variation in HU discussed herein, including differences in beam spectrum, body habitus, and/or beam hardening. It may be beneficial to include one or more inserts with uric acid and/or calcium oxalate or other stone material in the scan volume so that these effects can be assessed or removed as discussed elsewhere herein. Dual energy CT, as discussed elsewhere herein, may benefit from a phantom with inserts with different atomic properties, for example in this case calcium oxalate and uric acid crystals, so as to improve the accuracy or confidence in the determination of a dual energy CT imaging system. In addition, having in scan phantom inserts with related material may enable diagnosis with a lower radiation dose scan since noisier HU measurements will still be sufficient.

PET & PET-CT:

For PET scanning, a change in Standardized Uptake Value (SUV) is commonly used to characterize the response of a tumor to treatment. A problem that exists is that SUV can vary based upon many factors, including, for example, motion, attenuation correction, dose and system calibration, and time since administration of the dose. An in-scan phantom with one or more measured radioactive inserts as discussed herein can provide a known amount of radioactivity and allow compensation for, or recognition of, some of the sources of variation, other than inaccuracies of administered radiopharmaceutical dose or change in uptake duration between different scans. In addition, the benefits of CT in-scan phantoms apply to attenuation correction being done by CT.

PET-MR:

For PET-MR, the benefits mentioned above regarding use of an in-scan phantom for PET apply to PET-MR as well. In addition, there are benefits from using MR-active measured inserts, for example with different concentrations of MR contrast as discussed in "Improvements in Diagnostic Accuracy with Quantitative Dynamic Contrast Enhanced MRI; Pineda; Award Number: W81XWH-11-1-0042; REPORT DATE: December 2012" and "Kinetic Curves of Malignant Lesions Are Not Consistent Across MRI Systems: Need for Improved Standardization of Breast Dynamic Contrast-Enhanced MRI Acquisition;" Jansen et al; AJR:193, September 2009, both incorporated by reference. A third type of insert can include material and atoms to act similar to bone when performing a Dixon sequence or similar sequence for attenuation correction for the PET image. Because it is generally more difficult to do proper attenuation correction with MR than CT, having the radioactive PET insert may be even more valuable in PET-MR.

Although various embodiments have been described in detail for the purpose of illustration, it is to be understood that such detail is solely for that purpose and that the disclosure is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment.

The invention claimed is:

1. An in-scan phantom for use in an imaging procedure, the in-scan phantom comprising:
   a measured insert comprising a radioactive material that is configured to be non-uniform along a Z-axis of the in-scan phantom.

2. The in-scan phantom of claim 1, further comprising a second measured insert comprising at least one of a low density foam, an ultra-low density foam, an X-ray active gas, and water.

3. The in-scan phantom of claim 1, further comprising a measuring insert capable of measuring at least one of patient motion during the imaging procedure, and patient weight.

4. The in-scan phantom of claim 1, further comprising:
   an imaging modality system.

5. The imaging modality system of claim 4, wherein the imaging modality system is a combination imaging modality system selected from a PET/CT combined modality and a PET/MR combined modality.

6. The imaging modality system of claim 4, further comprising an auxiliary device system that receives information measured by the measuring insert of the in-scan phantom.

7. A method comprising:
   placing a patient within an imaging modality of an imaging modality system, wherein the imaging modality system also contains an in-scan phantom comprising a measured insert comprising a radioactive material that is configured to be non-uniform along a Z-axis of the in-scan phantom; and imaging the patient and the in-scan phantom using the imaging modality.

8. The method of claim 7, further comprising removing at least one measured insert from or inserting at least one measured insert into the in-scan phantom prior to imaging the patient and the in-scan phantom.

9. The method of claim 7, further comprising:
   performing a scout scan using the imaging modality.

* * * * *